(12) United States Patent
Brukilacchio

(10) Patent No.: US 7,488,102 B2
(45) Date of Patent: Feb. 10, 2009

(54) LED ILLUMINATOR FOR CHANGING TARGET PROPERTIES

(75) Inventor: Thomas J. Brukilacchio, Reading, MA (US)

(73) Assignee: Innovations In Optics, Inc., Woburn, MA (US)

( * ) Notice: Subject to any disclaimer, the term of this patent is extended or adjusted under 35 U.S.C. 154(b) by 153 days.

(21) Appl. No.: 11/593,964

(22) Filed: Nov. 7, 2006

(65) Prior Publication Data

US 2007/0053199 A1 Mar. 8, 2007

Related U.S. Application Data

(62) Division of application No. 10/334,525, filed on Dec. 30, 2002, now Pat. No. 7,153,015.

(51) Int. Cl.
*F21V 33/00* (2006.01)

(52) U.S. Cl. .................. 362/573; 362/555; 362/109; 433/29

(58) Field of Classification Search ................. 362/551, 362/555, 237, 240, 247, 608–610, 612, 613, 362/573, 109; 433/29
See application file for complete search history.

(56) References Cited

U.S. PATENT DOCUMENTS

| | | | |
|---|---|---|---|
| 4,367,519 A | 1/1983 | Houghton et al. |
| 4,915,479 A | 4/1990 | Clarke |
| 4,964,025 A | 10/1990 | Smith |
| 5,146,248 A | 9/1992 | Duwaer et al. |
| 5,255,171 A | 10/1993 | Clark |
| 5,289,356 A | 2/1994 | Winston |
| 5,335,152 A | 8/1994 | Winston |
| 5,335,158 A | 8/1994 | Kaplan et al. |
| 5,560,700 A | 10/1996 | Levens |
| 5,586,013 A | 12/1996 | Winston et al. |
| 5,699,201 A | 12/1997 | Lee |
| 5,810,469 A | 9/1998 | Weinreich |
| 5,816,693 A | 10/1998 | Winston et al. |
| 5,899,557 A | 5/1999 | McDermott |
| 6,123,436 A | 9/2000 | Hough et al. |
| 6,149,283 A | 11/2000 | Conway et al. |
| 6,200,002 B1 | 3/2001 | Marshall et al. |
| 6,257,737 B1 | 7/2001 | Marshall et al. |
| 6,272,269 B1 | 8/2001 | Naum |
| 6,465,961 B1 | 10/2002 | Cao |
| 6,641,284 B2 | 11/2003 | Stopa et al. |
| 6,784,603 B2 | 8/2004 | Pelka et al. |
| 2002/0114168 A1 | 8/2002 | Pelka et al. |
| 2002/0172039 A1 | 11/2002 | Inditsky |

OTHER PUBLICATIONS

Welford, W.T. and Winston, R., High Collection Nonimaging Optics, Academic Press, Inc. San Diego, 1989, pp. 213-215.

*Primary Examiner*—Thomas M Sember
(74) *Attorney, Agent, or Firm*—Francis J. Caufield

(57) ABSTRACT

An illuminator for irradiating targets to change their properties comprises at least one LED having spectral properties that are capable of interacting with a target to effect changes in its properties, a non-imaging concentrator for collecting radiation from the LED and emitting it as a spatially and spectrally uniform beam over a predetermined solid angle, and a light guide coupled to the exit aperture of the non-imaging concentrator to direct radiation to the target.

18 Claims, 5 Drawing Sheets

# LED ILLUMINATOR FOR CHANGING TARGET PROPERTIES

CROSS-REFERENCE TO RELATED APPLICATIONS

This application is a divisional of U.S. patent application Ser. No. 10/334,525 filed on Dec. 30, 2002 now U.S. Pat. No. 7,153,015 bearing the title, LED WHITE LIGHT OPTICAL SYSTEM, the entire contents of which is incorporated herein by reference.

FIELD OF THE INVENTION

This invention relates to a white-light optical system, and more particularly, to a LED white-light optical system that provides spatially uniform high intensity white light over a near field diverging region in a highly efficient manner.

BACKGROUND OF THE INVENTION

Many optical energy applications require high intensity, spatially uniform, white light that does not significantly heat the surrounding environment in the near field and/or far field. More specifically, many applications require correlated color temperatures between 4100-4900K (i.e., white light) with a color rendering index ("CRI") between 90 to 100.

Correlated color temperature ("CCT") is a numerical assignment of the apparent color of a light source (i.e., as viewed by the human visual system) and is measured in degrees Kelvin. Color rendering is how well a light source renders color (i. e., in the course of interacting with an object) as compared to how well daylight renders color (i.e., in the course of interacting with the same object).

Traditional light sources, however, suffer from, for example, but not limited to, combinations of a poor CRI, poor CCT, poor intensity, short usage life, large power electrical consumption, large package size, thermal energy, and/or are electrically and ; or optically inefficient.

Tungsten filament lamps. for example, while providing high intensity optical energy with high CRI values, emit optical energy that has a poor CCT (i.e., about 3000K. which correlates to the color yellow) for white light applications. In addition. tungsten filament lamps have a low electrical to optical efficiency and, thus, require large amounts of electrical power to generate high intensity optical energy, which results in large quantities of thermal energy. Furthermore. high power tungsten lamps have a low lamp lifetime, usually operating for about 500 hours.

Tungsten-halogen lamps, when used in conjunction with filters, produce a CCT of above 4000K but still suffer from many of the same disadvantages of Tungsten filament lamps.

Metal halide lamps have a high luminous efficiency ("electric energy" to "optical energy" efficiency) and produce optical energy with a CCT of around 5000K (bluish white), which is just above the white light range. However. Metal halide lamps also emit optical energy below and above the human visual system. The optical energy above the white light CCT range is referred to as infrared light. Infrared light optical energy is sensed as thermal energy or heat. The optical energy below the white light CCT range is referred to as ultra violet light and in many circumstances an unwanted or damaging byproduct. Xenon arc lamps provide optical energy with higher intensity than metal halide lamps. but have a low luminous efficiency and low lamp life time (around 500 hours). Furthermore, traditional light sources such as arc lamps, for example, when used as a light source for a less than spherical illumination region, are optically inefficient. The full spherical discharge of optical energy is difficult to capture into a particular illumination region.

A light emitting diode ("LED") emits optical energy over specific CCT's within the white light CCT range. However, commercially available LED's that emit white light have low CCT and have poor control. In addition, LED's provide insufficient optical energy for most illumination applications.

An improved optical system is needed.

SUMMARY OF THE INVENTION

A preferred embodiment of the invention provides a LED lighting device that produces high intensity, spatially uniform, white light in the near and far fields in a reduced package size that does not significantly heat the surrounding environment, wherein the white light is produced by using a phosphor layer in conjunction with a single LED.

An alternative embodiment of the invention provides a method for obtaining high intensity, spatially uniform, white light in the near and far fields in a reduced package size that does not significantly heat the surrounding environment, wherein the white light is produced by using a phosphor layer in conjunction with a single LED.

A preferred embodiment of the invention provides an LED curing device that produces high intensity, spatially uniform, optical energy for curing in the near and far fields in a reduced package size that does not significantly heat the surrounding environment, wherein the optical energy is produced by using single and multiple LED's.

A preferred embodiment of the invention provides a method for obtaining high intensity, spatially uniform, optical energy for curing in the near and far fields in a reduced package size that does not significantly heat the surrounding environment, wherein the optical energy is produced by using single and multiple LED's.

A preferred embodiment of the invention provides a LED photo-dynamic therapy device that produces high intensity, spatially uniform, optical energy for photo-dynamic therapy in the near and far fields in a reduced package size that does not significantly heat the surrounding environment, wherein the optical energy is produced by using single and multiple LED's and single and multiple concentrators.

A preferred embodiment of the invention provides a method for obtaining high intensity, spatially uniform, optical energy for photo-dynamic therapy in the near and far fields in a reduced package size that does not significantly heat the surrounding environment, wherein the optical energy is produced by using single and multiple LED's and single and multiple concentrators.

An alternative embodiment of the invention provides a LED illumination device that produces high intensity, spatially uniform, white light in the near and far fields in a reduced package size that does not significantly heat the surrounding environment, wherein the white light is produced by using an array of different color LEDs and single and multiple concentrators.

An alternative embodiment of the invention provides a method for obtaining high intensity, spatially uniform, white light in the near and far fields in a reduced package size that does not significantly heat the surrounding environment, wherein the white light is produced by using an array of different color LED's and single and multiple concentrators.

BRIEF DESCRIPTION OF THE DRAWINGS

Other features of the invention will become apparent from the following detailed description considered in connection with the accompanying drawings. It is to be understood, however, that the drawings are designed as an illustration only and not as a definition of the limits of the invention.

In the drawings, wherein similar reference characters denote similar elements through the several views.

DETAILED DESCRIPTION OF THE PREFERRED EMBODIMENT

Figure 1:
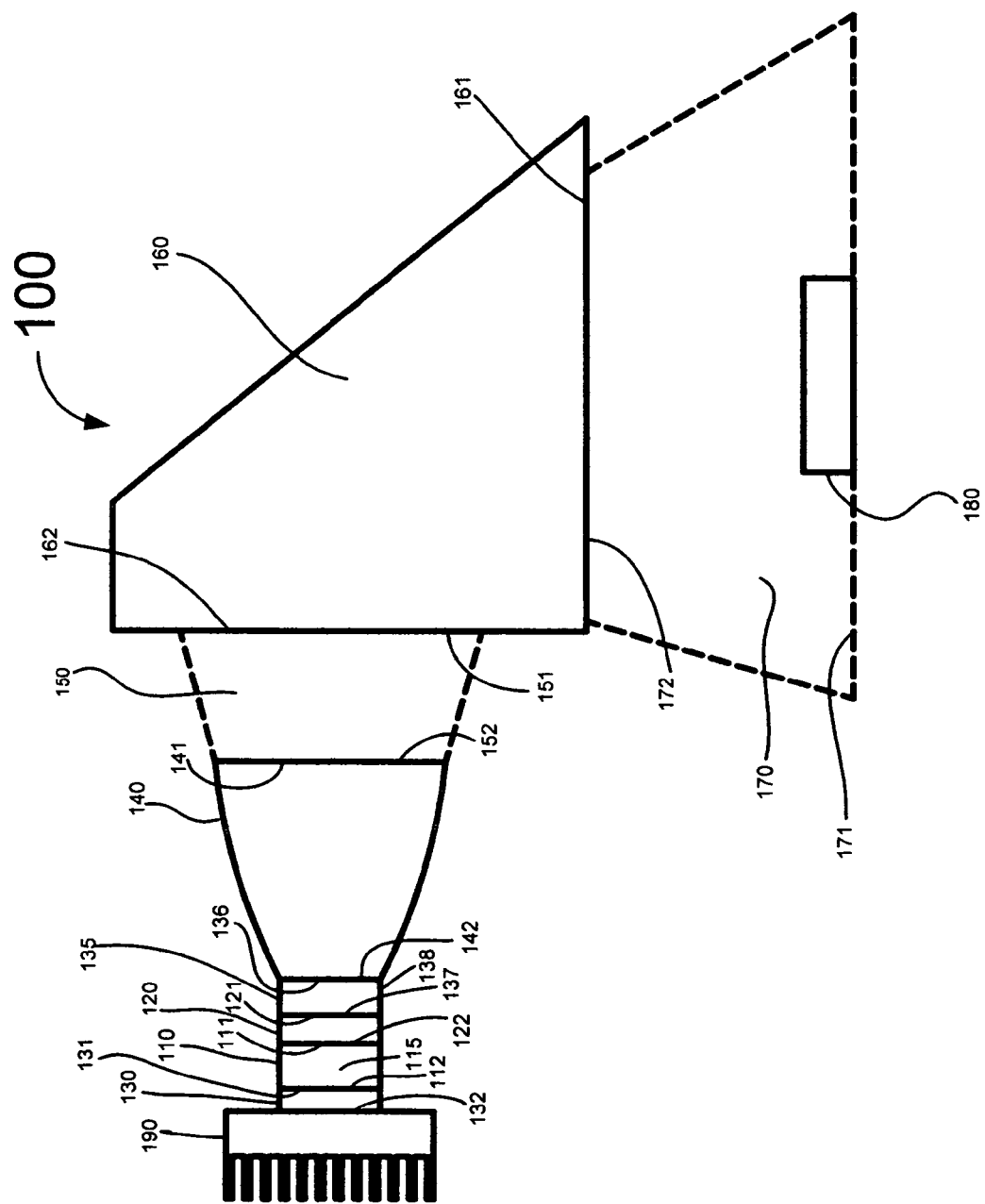
FIG. 1 illustrates a white light system according to a preferred embodiment of the invention.

Applications, including, but not limited to, indication, illumination, curing, photo-dynamic therapy, scanning, etc., require optical energy with specific characteristics, such as, but not limited to, wavelength spectrum, a CCT range, a CRI value, angular distribution, intensity, and/or spatial distribution, high electrical-to-optical power conversion efficiency, etc.

Optical energy, in general, includes the optical wavelength spectrum from 100 nanometers wavelength to 20 microns wavelength and includes the visual light spectrum, the infrared spectrum, and the ultraviolet light spectrum. The visual light spectrum is from 380 nanometers wavelength to 750 nanometers wavelength, the infrared spectrum is from 700 nanometers wavelength to 20 microns wavelength and the ultraviolet spectrum is from 100 nanometers to 380 nanometers. The wavelength spectrum or spectrum width of optical energy refers to the wavelengths present within the optical energy. A uniform wavelength spectrum occurs when the wavelength spectrum is the same spectrum at each point within a region of the optical energy.

Intensity of optical energy is defined as the power per unit area. Thus, the intensity of optical energy in a diverging illumination pattern will decrease as the distance from the optical energy source increases (i.e., since the unit area increases).

Spatial distribution of optical energy is the intensity (as defined as power per unit area) at each point in a particular target area relative to the entire illuminated area. Uniform spatial distribution occurs when the optical energy per unit area is constant.

Angular distribution is the direction of the emitted optical energy. For example, the sun emits light over the entire area of the sun's surface. The area of a sphere equals $4\pi$ times the square of the radius. In optics, this is referred to as $4\pi$ steradians for a sphere and $2\pi$ steradians for a hemisphere. Thus the angular distribution of the sun is $4\pi$ steradians: However. light sources, other than the sun, emit light at less than $4\pi$ steradian, due to the geometry of creating or delivering the optical energy. An LED emits optical energy out the face (when the LED is encapsulated) of the LED into a hemisphere (i. e., $2\pi$ steradian).

Also, optical energy is defined as being in the near field or the far field. Optical energy is referred to as near field if the region of interest is within ten times the diameter of the source. Thus for an optical element with an exit aperture of ten millimeters, the near field is the region within 100 millimeters of the exit aperture and the far field is the region past 100 millimeters.

Optical energy systems utilize optical elements to manipulate, direct, filter, etc. optical energy to better prepare the optical energy for a particular application. Thus, between the optical energy source and the end application there may be multiple optical elements. Optical elements include any element capable of interacting with optical energy and can include elements such as, but not limited to, filters, reflectors, diffractors, refractors, aligners, lenses, concentrators, polarizers, micro-structures, etc. Four characteristics of an optical interaction include scatter, transmission, fluorescence and phosphorescence, absorption and reflection of the optical energy.(i.e., photons).

Thus for example, optical energy interacting with a filter will scatter a percentage of the optical energy, transmit through the filter a percentage of optical energy, absorb a percentage of the optical energy, and reflect a percentage of the optical energy. The magnitude of these percentages is a function of the optical energy and of the filter.

Optical efficiency is the ratio of total optical power that reaches a desired target area to the total optical power initially received and/or created by a given optical system.

A preferred embodiment of the invention increases optical efficiency over conventional optical systems by utilizing index matching. The optical efficiency of an interface between a first and second medium is potentially affected by the index of refraction of each medium. Everything from air to optical element materials have an associated index of refraction. In order for there not be any optical energy loss, due to total internal reflection, the index of refraction of the second element must be equal to or less than the index of refraction of the first element, referred to as index matching. When there is no index matching, the amount of optical energy passed from the first element to the second element is reduced, thereby reducing the optical efficiency.

A preferred embodiment of the invention increases optical efficiency over conventional optical systems by utilizing flush connections. The optical efficiency of an interface between a first and second medium is potentially affected by flushness of the physical interface connection. Two optical elements are flush if there are no impurities or irregularities between the two attaching surfaces (also referred to as being in optical contact). A flush connection allows the optical energy to pass from one medium to a second medium without any loss of optical efficiency.

A preferred embodiment of the invention increases optical efficiency over conventional optical systems by geometrically matching optical elements. The optical efficiency of an interface between a first and second medium is potentially affected by the geometric shapes of each medium. A second medium entrance aperture shape that is the same or larger than a first medium exit aperture shape ensure that all the optical energy, when transmitting from a first medium exit aperture is captured by the second medium entrance aperture.

Referring to the drawings and in particular to FIGS. 1-5, there are shown preferred embodiments of the invention.

FIG. 1 illustrates a white light system 100 according to a preferred embodiment of the invention. The optical system 100 includes a LED optical source 110, an optical filter 120, a reflector 130, a phosphor layer 135, a concentrator 140, a first illumination region 150, a secondary optical element 160, a second illumination region 170, a target 180, and a thermal dissipater 190.

The LED optical source 110 provides optical energy. The LED optical source 110 includes optical material 115 with a front face 111 and back face 112.

Electrical current is provided to the LED by power source (not shown). An LED provides optical energy at particular CCT ranges. When an electrical field is applied across a LED semiconductor junction, photons are released within the semiconductor material. The Photons emit in a 4π steradian angular distribution and exit the LED via the front and back face. The semiconductor material determines the CCT range of the created optical energy.

In a preferred embodiment of the invention, the LED optical source front face 111 emits optical energy over a 2π steradian distribution. In an alternative embodiment of the invention, the LED optical source back face 112 emits optical energy over a 2π steradian distribution.

In an alternative embodiment of the invention, LED optical source 110 is thermally connected to the thermal dissipater 190. In an alternative embodiment, LED optical source 110 is any source that emits optical energy at the desired CCT range, at the desired optical energy level and over a 2π steradian distribution.

In a preferred embodiment of the invention, the LED optical source front face 111 surface area is flat. In a preferred embodiment of the invention, the LED optical source front face 111 surface area is circular. In an alternative embodiment of the invention, the LED optical source front face 111 surface area is square. In a preferred embodiment of the invention, the LED optical source back face 112 surface area is flat. In a preferred embodiment of the invention, the LED optical source back face 112 surface area is circular. In a preferred embodiment of the invention, the LED optical source back face 112 surface area is square.

Optical energy (i.e., photons) are created by a light emitting diode ("LED") by the injection of electrical current into a semiconductor junction. The electrical current is injected by an electrical power source such as, but not limited to, an electrical wall plug, a battery, a fuel cell, a generator, etc. The selection of LED semiconductor material for the p and n type junctions determines the CCT range of the created optical energy emitted from the LED and dictates the amount of thermal energy produced by the LED as a result of the creation of optical energy from electrical energy.

In an alternative embodiment of the invention, LED optical source 110 can be any light source that produces optical energy. In an alternative embodiment of the invention, LED optical source 110 is an array of LEDs. In an alternative embodiment of the invention, LED optical source 110 is an array of nine LEDs placed in close proximity to each other.

In an alternative embodiment of the invention, electrical current is delivered to the LED semiconductor junction within the LED material 115 through a wire that connects a bond pad, which is positioned at the semiconductor junction on the LED, to electrically conducting gold posts, which pierce (or go through) a header. A header mounts or attaches the LED. In a preferred embodiment. the header attaches the LED to the heat dissipater 190. The bond pad is the contact point for injecting electrical current into the semiconductor junction and the wire is an aluminum wire 0.0025 inches in diameter. The gold posts electrically attach to the electrical power source.

In an alternative embodiment, an electrically conducting material is positioned on the LED optical source back face 112. In an alternative embodiment of the invention, the electrically conducting material is a gold plate positioned on the LED optical source back face 112. In an alternative embodiment; the cathode (or negative polarity) is positioned on the LED optical source back face 112. In an alternative embodiment, the anode (or positive polarity) is positioned on the LED optical source front face 111.

In an alternative embodiment, an encapsulating layer is positioned on the LED optical source front face 111. The encapsulate protects the aluminum wires from external forces that may cause the electrical connection to break. In an alternative embodiment, the encapsulate is Masterbond UV 15-7.

In a preferred embodiment of the invention, the index of refraction of the encapsulate is the same as the index of refraction of the phosphor layer 135. In an alternative embodiment, the index of refraction of the encapsulate is greater than the index of refraction of the phosphor layer 135. In a preferred embodiment of the invention, the index of refraction of the encapsulate is the same as the index of refraction of the concentrator 140. In an alternative embodiment, the index of refraction of the encapsulate is greater than the index of refraction of the phosphor layer 135.

In FIG. 1, electrical power is supplied to the LED optical source 110 by a power source. The power source is electrically attached to LED optical source 110. In a preferred embodiment of the invention, the power source is a battery. In a preferred embodiment of the invention, the power source is an electrical wall socket. In a preferred embodiment of the invention, the power source is a fuel cell.

In FIG. 1, reflector 130 is a reflective optical element positioned to reflect optical energy emitted from the LED optical source back face 112 back into the LED optical source 110. The reflector has a front face 131 that reflects optical energy and a back face 132 that attaches to thermal dissipater 190. In a preferred embodiment of the invention, the reflector reflects optical energy back into the LED optical material 115 through the LED back face 112. The optical energy then interacts with the optical material and a portion of the optical energy will exit LED front face 111 and interacts with the optical filter 120. In a preferred embodiment of the invention, the reflector 130 is a mirror. In an alternative embodiment of the invention, reflector 130 filters out optical energy in the infrared spectrum.

In a preferred embodiment of the invention, the reflector 130 is an optical coating applied directly onto the LED optical source back face 112. In a preferred embodiment of the invention, the reflector 130 is an optical coating applied directly onto the thermal dissipater 190. In a preferred embodiment of the invention, the reflector 130 reflects optical energy at a CCT range of 6000K to 8000K.

In a preferred embodiment of the invention, the reflector front face 131 is flush with the LED optical source back face 112. In a preferred embodiment, the reflector front face 131 surface area shape geometrically corresponds to the LED optical source back face 112 surface area shape. In an alternative embodiment of the invention, the reflector front face 131 surface area shape is larger than the LED optical source back face 112 surface area shape. In an alternative embodiment of the invention, the reflector front face 131 is smaller than the LED optical source back face 112 surface area shape.

In a preferred embodiment of the invention, the reflector front face 131 surface area is flat. In a preferred embodiment of the invention, the reflector back face 132 surface area is flat. In a preferred embodiment of the invention, the reflector front face 131 surface area shape is circular. In a preferred embodiment of the invention, the reflector back face 132 surface area is circular.

In FIG. 1, the optical filter 120 is positioned after LED optical source front face 111. Optical filter 120 includes a front face 121 and a back face 122. The optical energy emitted from LED optical source front face 111 enters optical filter back face 122 and interacts with optical filter 120. The optical energy is then reflected back out optical filter back face 122 or transmitted through optical filter front face 121, notwithstanding the slight amount of optical energy that is scattered and/or absorbed.

The optical filter 120 includes a reflected CCT range and a transmitted CCT range. Optical energy that is within the reflected CCT range is prohibited from passing through the optical filter 120 (e.g., via reflection). Optical energy that is within the transmitted CCT range passes through the optical filter 120. In a preferred embodiment of the invention, the optical filter 120 transmits optical energy at a CCT range of 6000K to 8000K and reflects optical energy at a CCT range of 2500K to 6000K.

In a preferred embodiment of the invention, the optical filter front face 121 emits optical energy over a two pi steradian distribution. In a preferred embodiment of the invention, the optical filter back face 122 emits optical energy substantially over a two pi steradian distribution.

In a preferred embodiment of the invention, the optical energy spatial distribution emitted through optical filter front face 121 is uniform. In a preferred embodiment of the invention, the optical energy spatial distribution emitted through optical filter back face 122 is uniform.

In a preferred embodiment, the optical filter back face 122 is flush with the LED optical source front face 111. A flush connection allows the optical filter back face 122 to capture two pi steradian angular distribution of optical energy from the LED optical source front face 111.

In a preferred embodiment of the invention, the optical filter 120 is an optical coating. In an alternative embodiment of the invention, the optical filter 120 is a dielectric stack coated directly onto the LED optical source front face 111.

In a preferred embodiment of the invention, the optical filter back face 122 surface area is flat. In a preferred embodiment of the invention, the optical filter back face 122 surface area is circular. In an alternative embodiment of the invention, the optical filter back face 122 surface area is square. In a preferred embodiment of the invention, the optical filter front face 121 surface area is flat. In a preferred embodiment of the invention, the optical filter front face 121 surface area is circular. In a preferred embodiment of the invention, the optical filter front face 121 surface area is square.

In a preferred embodiment, the optical filter back face 122 surface area shape geometrically corresponds to the LED optical source front face 111 surface area shape. A geometrically corresponding connection allows the optical filter back face 122 to interact with all of the optical energy being emitted from the LED optical source front face 111. In an alternative embodiment of the invention, the optical filter back face 122 surface area shape is larger than the LED optical source front face 111 surface area shape. In an alternative embodiment of the invention, the optical filter back face 122 is smaller than the LED optical source front face 111 surface area shape.

In a preferred embodiment, the filter includes a stack of one fourth of the wavelength of light layers of alternating high and low refractive index to create the desired filtering characteristics.

In an alternative embodiment of the invention, the surface area shape of the optical Filter 120, in reference to the concentrator 140, is optimized to reflect particular CCT ranges. CRI values, and/or intensity values required in the first and/or second illumination regions.

In FIG. 1, the phosphor layer 135 is positioned to capture optical energy emitted from the optical filter front face 121. The phosphor layer 135 includes a back face 137, which receives optical energy from optical filter front face 121, a front face 136, which emits optical energy into said concentrator 140, and sides 138.

The phosphor layer 135 comprises material that when stimulated by optical energy of a particular CCT range (i.e., the stimulated CCT range), creates and emits new optical energy at a different CCT range (i.e., the phosphor-created CCT range) and, at the same time, allows non-stimulated optical energy (i. e., the non-stimulated CCT range) to transmit through the phosphor layer. In addition, the phosphor layer 135, as an optical element, allows a certain percentage of optical energy of the stimulated CCT range (i. e., that is not absorbed by the phosphor) to transmit through the phosphor layer (i.e., due to scattering).

Phosphor layer characteristics, such as, but not limited to, the amount of phosphor doping, the spectrum involved, and the thickness of the phosphor layer all affect the intensity and the wavelength spectrum that is emitted by the phosphor layer. The interaction of optical energy with the phosphor layer is an isotropic process resulting in an optical energy being emitted over a $4\pi$ distribution. Thus, optical energy emits out the phosphor layer back face, 137, the front face 136, and the sides 138.

In a preferred embodiment, optical energy enters the phosphor layer back face 137 and the optical energy within the stimulated CCT range, stimulates the phosphor within the phosphor layer 135 creating new optical energy within a phosphor-created CCT range. The new optical energy within the phosphor-created CCT range, when combined with optical energy that enters the phosphor layer back face 137 that is in the non-stimulated CCT range provides optical energy that corresponds to white light. In a preferred embodiment of the invention, optical energy emits from phosphor layer front face 136 that corresponds to white light on the CCT range.

In an alternative embodiment of the invention, the phosphor layer characteristics are modified or adjusted to ensure optical energy of a specific CCT range emits from phosphor layer front face 136.

A small percentage of optical energy is emitted out of the sides 138 of the phosphor layer (i.e., side loss). In a preferred embodiment of the invention, the amount of side loss is decreased by coating the interior side wall with a reflective material. In an alternative embodiment of the invention, the amount of side loss is decreased by reducing the surface area of the sides. In an alternative embodiment of the invention, side loss is reduced by placing the sides in contact with a medium of lower refractive index.

In a preferred embodiment of the invention, optical energy emitting from the phosphor layer back face 137 enters the optical filter 120 through the optical filter back face 122. The optical filter 120 includes a reflected CCT range and a transmitted CCT range. Optical energy that is within the reflected CCT range is prohibited from passing through the optical filter 120 (e.g., via reflection). Optical energy that is within the transmitted CCT range passes through the optical filter 120. Accordingly, the optical energy that enters the optical filter front face 121 from the phosphor layer back face 137 that is in the optical filter 120 reflected CCT range will be reflected back into the phosphor layer 135 and the optical energy that is in the optical filter 120 transmitted CCT range will transmit through the optical filter 120 and into the LED optical source 110, but for losses associated with absorption and scattering.

In a preferred embodiment of the invention, the optical energy that enters the optical filter 120 from the phosphor layer 135 that is in the optical filter 120 transmitted CCT range transmits through the optical filter 120 and into the LED optical source 110 and then interacts with the optical reflective element 130. At that point, the optical energy is reflected back into the LED material 115 and then transmits to the optical filter 120. Since the optical energy is within the optical filter transmission wavelength spectrum, the optical energy passes through the filter and into the Phosphor Layer. whereupon the optical energy interacts with the phosphor layer thereby providing a repeating telescoping circular process for the optical energy that emits out of the phosphor layer back face 137. This repeating process captures optical energy that would otherwise be lost.

In a preferred embodiment of the invention, the Phosphor layer 135 is Phosphor Technologies Yttrium Aluminum Oxide: Cerium QMK58/F-U1. In a preferred embodiment of the invention, the phosphor layer 135 is 0.254 millimeters thickness. In a preferred embodiment of the invention, the phosphor layer stimulated CCT range is 6000K to 8000K. In a preferred embodiment of the invention, the phosphor layer phosphor created CCT range is 2500K to 6000K.

In a preferred embodiment of the invention, the spatial distribution of the optical energy emitted through the phosphor layer front face 136 is uniform. In a preferred embodiment of the invention, the spatial distribution of the optical energy emitted through the phosphor layer back face 137 is uniform.

In a preferred embodiment, the phosphor layer back face 137 is flush with the optical filter front face 121. In a preferred embodiment, the phosphor layer back face 137 surface area shape geometrically corresponds to the optical filter front face 121 surface area shape. In an alternative embodiment of the invention, the phosphor layer back face 137 surface area shape is larger than the optical filter front face 121 surface area shape. In an alternative embodiment of the invention, the phosphor layer back face 137 is smaller than the optical filter front face 121 surface area shape.

In a preferred embodiment of the invention, the phosphor layer front face 136 surface area is flat. In a preferred embodiment of the invention, the phosphor layer back face 137 surface area is flat. In a preferred embodiment of the invention, the phosphor layer front face 136 surface area shape is circular. In a preferred embodiment of the invention, the phosphor layer back face 137 surface area shape is circular.

In an alternative embodiment of the invention, the thickness of the phosphor layer is optimized to stimulate particular CCT ranges, CRI values, and/or optical energy values required in the first and/or second illumination regions. In an alternative embodiment of the invention, the surface area shape of the phosphor layer 135, in reference to the concentrator 140, is optimized to stimulate particular CCT ranges, CRI values, and/or optical energy values required in the first and/or second illumination regions.

In FIG. 1, the concentrator 140 is positioned to capture optical energy emitting out of the phosphor layer front face 136. The concentrator 140 has an entrance aperture 142, which receives optical energy from the phosphor layer front face 136, and an exit aperture 141, which outputs optical energy into the first illumination region 150. The concentrator 140 captures optical energy up to a two pi steradian distribution via the entrance aperture 142, aligns the optical energy via total internal reflection, and then outputs the aligned optical energy through the exit aperture 142 into a three dimensional symmetrical pattern or region, referred to as the first illumination region 150.

In a preferred embodiment of the invention, the concentrator entrance aperture 142 is fully filled. In a preferred embodiment of the invention, the concentrator exit aperture 142 is fully filled. The entrance aperture is fully filled when entrance aperture receives optical energy over the entire entrance aperture.

In a preferred embodiment, the concentrator 140 is a non-imaging concentrator. A non-imaging concentrator provides a diverging illumination pattern. A concentrator provides a high degree of light collection. The theoretical throughput performance of a circular non-imaging concentrator is one hundred percent collection efficiency and close to ninety six percent of the collected optical energy exits through the exit aperture within the solid angle as defined by the concentrator physical characteristics. The approximate four percent loss is attributed to rim loss. A trough concentrator approaches 100 % efficiency. The ideal profile of a non-imaging concentrator is a compound parabola, which is referred to as a compound parabolic concentrator ("CPC"). In a preferred embodiment of the invention, concentrator 140 is a CPC. In a preferred embodiment of the invention, the profile of concentrator 140 is determined by the angular illumination region requirements of the optical system. The reference Welford, Winston, "High Collection Nonimaging Optics", Academic Press, Inc. '89, ISBN 0-12-742885-2, which is hereby incorporated by reference, provides a detailed discussion of nonimaging optics.

Non-imaging concentrators maintain etundue. The etundue formula holds that the input numerical aperture multiplied by the input optical energy spatial extent equals the output numerical aperture multiplied by the output optical energy spatial extent.

In an alternative embodiment of the invention, the non-imaging concentrator has a profile constructed with a high order polynomial surface representing the attributes of the non-imaging concentrator form. In an alternative embodiment of the invention, the aspheric sag equation is tuned to match an appropriate non-imaging concentrator. In an alternative embodiment, the circumference of the concentrator is faceted. The higher the number of facets, the closer the faceted concentrator comes to producing the results of a circular concentrator. In a preferred embodiment of the invention, the concentrator emits optical energy with a CCT range of 4100K to 4900K. In a preferred embodiment of the invention, the concentrator emits optical energy that corresponds to white light according to the human visual system. In a preferred embodiment of the invention, the spatial distribution of the optical energy emitted through the non-imaging concentrator exit aperture 142 is uniform.

In a preferred embodiment of the invention, the concentrator entrance aperture 141 is flush with the phosphor layer front face 136. In a preferred embodiment of the invention, the concentrator entrance aperture 142 surface area shape geometrically corresponds to the phosphor layer front face 136 surface area shape. In an alternative embodiment of the invention, the concentrator entrance aperture 142 surface area shape is larger than the phosphor layer front face 136 surface area shape. In an alternative embodiment of the invention, the concentrator entrance aperture 142 is smaller than the phosphor layer front face 136 surface area shape.

In a preferred embodiment of the invention, the index of refraction of the concentrator 140 is the same as the index of refraction of the phosphor layer 135. In an alternative embodiment, the index of refraction of the concentrator 140 is less than the index of refraction of the phosphor layer 135.

In a preferred embodiment of the invention, the concentrator entrance aperture 142 surface area is flat. In a preferred embodiment of the invention, the concentrator exit aperture 141 surface area is flat. In a preferred embodiment of the invention, the concentrator entrance aperture 142 surface area shape is circular. In a preferred embodiment of the invention, the concentrator exit aperture 141 surface area shape is circular.

In FIG. 1, the first illumination region 150 is positioned to receive optical energy emitted from the concentrator 140. The optical energy that emits from the concentrator 140 has a corresponding angular distribution. This angular distribution of the optical energy forms diverging angles that define the first illumination region 150. The first illumination region 150 has a first illumination region back face 152, which defines the beginning area of the first illumination pattern, and a first illumination region front face 151, which defines the end area of the first illumination patter. In a preferred embodiment of the invention, the first illumination region 150 is a diverging conical three-dimensional region and is defined by the angular distribution characteristics associated with concentrator 140.

The first illumination region 150 is located in a first illumination medium. In a preferred embodiment of the invention, the first medium is air. In a preferred embodiment of the invention, the first illumination medium does not require sides to bound or to direct the optical energy in the first illumination region since the optical energy in first illumination region is aligned.

In a preferred embodiment of the invention, the index of refraction of the first medium has a value of one. In a preferred embodiment of the invention, the index of refraction of the first medium is the same as the index of refraction of the concentrator 140. In an alternative embodiment of the invention, the index of refraction of the first medium is less than the index of refraction of the concentrator 140. In a preferred embodiment of the invention, the first illumination region 150 contains optical energy with a CCT range of 4100K to 4900K. In a preferred embodiment of the invention, the first illumination region front face 151 emits optical energy with a CCT range of 4100K to 4900K. In a preferred embodiment of the invention, the first illumination region contains optical energy that corresponds to white light according to the human Visual system. In a preferred embodiment of the invention, the first illumination region front face 151 emits optical energy that corresponds to white light according to the human visual system. In a preferred embodiment of the invention, the spatial distribution of the optical energy emitted through the first illumination region front face 152 is uniform.

In FIG. 1, the secondary optical element 160 is positioned to receive optical energy from the first illumination front face 151. The secondary optical element 160 includes a back face 162, which receives optical energy from the first illumination region 150 via first illumination front face 151, and a front face 161, which emits optical energy to a second illumination region 170.

In a preferred embodiment of the invention, the secondary optical element 160 is a prism: and re-directs the aligned optical energy present in the first illumination region 150 to a second illumination region 170. In a preferred embodiment of the invention, optical element 160 is positioned within the near field of the concentrator 140.

In an alternative embodiment, secondary optical element 160 is any optical element that alters the optical energy present in the first illumination region 150. Optical elements include, but are not limited to, a prism, lens, filter, concentrator, mirror, refractive element, diffractive element, wavelength modifier, phosphorous layer, intensity modifier, light pipe, etc. Optic energy can be altered according to, for example, but not limited to, spatial distribution, wavelength spectrum, intensity and angular distribution.

In a preferred embodiment of the invention, the secondary optical element back face 162 is flush with the first illumination region front face 151. In a preferred embodiment of the invention, the secondary optical element back face 162 surface area shape geometrically corresponds to the first illumination region front face 151 surface area shape. In an alternative embodiment of the invention, the secondary optical element back face 162 surface area shape is larger than the first illumination region front face 151 surface area shape. In an alternative embodiment of the invention, secondary optical element back face 162 is smaller than the first illumination region front face 151 surface area shape.

In a preferred embodiment, the index of refraction of the secondary optical element 160 is the same as the index of refraction of the first medium. In an alternative embodiment, the index of refraction of the secondary optical element 160 is less than the index of refraction of the first medium.

In an alternative embodiment of the invention, the secondary optical element entrance aperture 162 is positioned to receive optical energy from the concentrator exit aperture 141. The optical energy that enters the secondary optical element has an angular distribution as defined by the geometric shape of the concentrator.

In a preferred embodiment of the invention, the secondary optical element back face 162 is flush with the concentrator exit aperture 141. In a preferred embodiment of the invention, the secondary optical element back face 162 surface area shape geometrically corresponds to the concentrator exit aperture 141 surface area shape. In an alternative embodiment of the invention, the secondary optical element back face 162 surface area shape is larger than the concentrator exit aperture 141 surface area shape. In an alternative embodiment of the invention, secondary optical element back face 162 is smaller than the concentrator exit aperture 141 surface area shape.

In a preferred embodiment, the index of refraction of the secondary optical element 160 is the same as the index of refraction of the concentrator 140. In an alternative embodiment, the index of refraction of the secondary optical element 160 is less than the index of refraction of the concentrator 1140.

In a preferred embodiment of the invention, the secondary optical element back face 162 surface area is flat. In a preferred embodiment of the invention, the secondary optical element front face 161 surface area is flat.

In a preferred embodiment of the invention, the secondary optical element back face 161 Surface area shape corresponds to the surface area of the interface between the illumination region and the secondary optical element back face 161. In a preferred embodiment of the invention, the secondary optical element back face 162 surface area shape is circular. In a preferred embodiment of the invention, the secondary optical element front face 161 surface area shape is circular. In a preferred embodiment of the invention, the secondary optical element back face 162 surface area shape is oval. In a preferred embodiment of the invention, the secondary optical element front face 161 surface area shape is oval.

In an alternative embodiment of the invention, when the secondary optical element 160 is a reflector, optical energy reflects off of the secondary optical element back face 162 and is redirected into a different direction, such as, but not limited to, back into the concentrator 140, back into the first illumination region 150, into a second illumination region 170, and/or into a second illumination region 170 that partially overlaps the first illumination region 150.

In a preferred embodiment of the invention, the secondary optical element front face 161 emits optical energy with a CCT range of 4100K to 4900K. In a preferred embodiment of the invention, the secondary optical element back face 162 reflects optical energy with a CCT range of 4100K to 4900K. In a preferred embodiment of the invention, the secondary optical element front face 161 emits optical energy that corresponds to white light according to the human visual system. In a preferred embodiment of the invention, the secondary optical element back face 162 reflects optical energy that corresponds to white light according to the human visual system. In a preferred embodiment of the invention, the spatial distribution of the optical energy emitted from the secondary optical element front face 162 is uniform.

In Figure I, the second illumination region 170 is positioned to receive optical energy emitted (and/or reflected) from the secondary optical element 141. The optical energy that emits (and/or reflects) from the secondary optical element 141 has a corresponding angular distribution. The angular distribution of the optical energy forms diverging angles that define the second illumination region 170. The second illumination region 170 has a second illumination region back face 172, which defines the beginning area of the second illumination pattern, and a second illumination region front face 171, which defines the end area of the second illumination pattern and is also referred to as the target area. In an alternative embodiment, the second illumination pattern extends past the target area. In a preferred embodiment of the invention, the second illumination region 170 is a diverging conical three dimensional region and is defined by the angular distribution characteristics associated with secondary optical element 160.

The second illumination region 170 is located in a second illumination medium. In a preferred embodiment of the invention, the second medium is air. In a preferred embodiment of the invention, the second illumination medium does not require sides to bound or to direct the optical energy in the second illumination region since the optical energy in second illumination region is aligned.

In a preferred embodiment of the invention, the index of refraction of the second medium has a value of one. In a preferred embodiment of the invention, the index of refraction of the second medium is the same as the index of refraction of the secondary optical element 160. In an alternative embodiment of the invention, the index of refraction of the second medium is less than the index of refraction of the secondary optical element 160.

In a preferred embodiment of the invention, the second illumination region 170 contains optical energy with a CCT range of 4100K to 4900K. In a preferred embodiment of the invention, the second illumination region front face 171 emits optical energy with a CCT range of 4100K to 4900K to a target 180. In a preferred embodiment of the invention, the second illumination region contains optical energy that corresponds to white light according to the human visual system. In a preferred embodiment of the invention, the second illumination region front face 171 emits optical energy that corresponds to white light according to the human visual system to a target 180. In a preferred embodiment of the invention, the spatial distribution of the optical energy emitted from the second illumination region front face 172 to a target 180 is uniform.

In a preferred embodiment of the invention, the second medium is flush with the secondary optical element front face 161. In an alternative embodiment of the invention, the second medium is flush with the secondary optical element back face 162.

In FIG. 1, the target 180 is positioned at the second illumination region front face 171. Optical energy present at the second illumination front face 171 interacts with the target 180 and reflects to the human visual system. In an alternative embodiment of the invention, the target 180 is located within the second illumination region 170.

In FIG. 1, the thermal dissipater 190 is thermally attached to the LED optical source 110. The thermal dissipater 190 dissipates thermal energy present in the white light system 100. In an alternative embodiment of the invention, the thermal dissipater 190 is thermally attached at any place in the white light system 100, including, but not limited to the LED optical source 110, the power source, the optical reflector 130, the optical filter 120, the phosphor layer 135, the concentrator 140, the first illumination region 150, the first medium, the secondary optical element 160, the second illumination region 170, the second medium, and/or the target 180, etc.

Thermal energy results from the creation of photons from electricity. In addition, optical energy within the infrared spectrum provides thermal energy. Infrared radiation has longer wavelengths than the visible spectrum and is sensed as thermal energy or heat.

In an alternative embodiment of the invention, an intercepting optical element, such as, but not limited to, a filter, a reflector, or absorber, etc., is positioned within white light system 100 to intercept optical energy in the infrared system. The thermal dissipater 190 is then thermally attached to this intercepting optical element.

In a preferred embodiment, the heat dissipater 190 is a heat sink. In an alternative embodiment of the invention, a header (not shown) is used to mount or attach the LED optical source 110 to the heat dissipater 190. In an alternative embodiment of the invention, the header is thermally conductive, thereby allowing thermal energy present in the LED optical source to transfer to the heat dissipater 190.

In an alternative embodiment, the header is electrically conductive, thereby providing an electrical connection for electrical power to reach the LED optical source 110. In an alternative embodiment of the invention, the header material includes copper. In an alternative embodiment of the invention, the header is formed into a thin cylinder.

In an alternative embodiment, the heat dissipater includes fins. The fins increase the surface area of the heat dissipater, which increases thermal dissipation.

In an alternative embodiment of the invention, a heat spreader is positioned between the heat sink and the LED optical source 110. The heat spreader is thermally attached to the LED optical source 110 and pulls the thermal energy away from the thermal energy source and disburses the thermal energy laterally (i.e., the LED optical source 110). Increased thermal dissipation provides for increased electric efficiency within the LED. In an alternative embodiment of the invention, the heat spreader material includes diamond. Diamond has a high thermal conductivity and thus permit higher operating currents to be used without increasing the temperature of the LED. In an alternative embodiment of the invention, the heat spreader material includes any material with a high conductivity, such as, but not limited to copper, aluminum, etc. The heat spreader is thermally attached to the thermal dissipater 190 and/or the heat sink.

Figure 2:
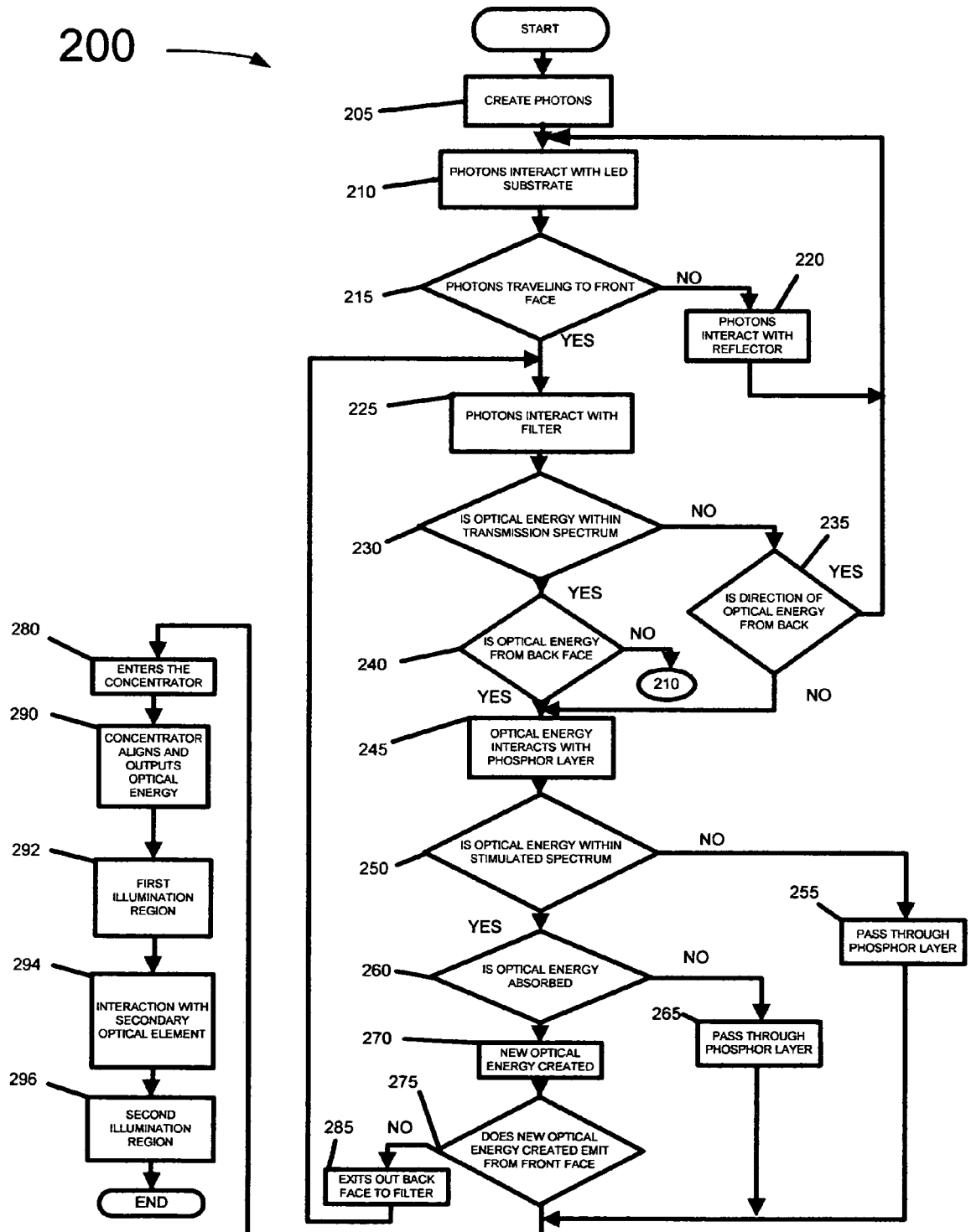
FIG. 2 illustrates a flow diagram of the white light system according to a preferred embodiment of the invention.

FIG. 2 illustrates a flow diagram of the white light system according to a preferred embodiment of the invention. Referring to the elements illustrated in FIG. I, in the first step. (step 205) a light source provides optical energy at a particular spectrum. In a preferred embodiment of the invention, the light source is an LED optical source 110, which creates photons when a current field is applied across the LED semiconductor junction. In a preferred embodiment of the invention, the created photons have a $4\pi$ steradian angular distribution. In a preferred embodiment of the invention, the electric power is provided to the LED optical source by a power source. The thermal energy produced by the LED optical source is dissipated by a thermal dissipater 190. In a preferred embodiment of the invention, the thermal dissipater is a heat sink, which dissipates the heat. In an alternative embodiment of the invention, a header (not shown) is used to attach the heat sink to the LED optical source. In an alternative embodiment of the invention, a heat spreader (not shown) is used to distribute the thermal energy from the LED optical source to the heat sink. In a preferred embodiment of the invention. the white light system 100 merges the optical energy created by the LED optical source and the optical energy created by the phosphor layer 135 to produce white light.

In the next step, (step 210) the photons interact within the LED semiconductor junction. The photons within the semiconductor junction emit in the direction of the LED optical source back face 112 and in the direction of the LED optical source front face 111. There is some loss due to optical scattering and absorption.

It is next determined (step 215) whether the photons in the LED are traveling toward the LED optical source back face 112. The photons that reach the LED optical source back face 112 interact with a reflector 130 (step 220) and the photons that are within the reflected spectrum are reflected back into the LED optical source 110 (step 210). Since the reflected optical energy is traveling in a direction towards the LED optical source front face 111, the reflected optical energy has a high probability of reaching the LED optical source front face 111. Thus, the optical efficiency of the white light system 100 is improved by the addition of a reflector to capture otherwise lost optical energy. In an alternative embodiment of the invention, the reflected spectral width is tailored to optimize the production of white light by the white light system 100.

The photons that reach the LED optical source front face 111 interact with an optical filter 120 (step 225). The optical filter 120 has a reflected spectral width and a transmitted spectral width. The optical energy that is within the reflected spectral width is reflected out of the face the optical energy interfaced the filter. The optical energy that is within the transmitted spectral width is transmitted through the optical filter. In a preferred embodiment of the invention, the optical filter 120 is coated directly onto the LED front face 111. In an alternative embodiment of the invention, the reflected spectral width and the transmitted spectral width is tailored to optimize the production of white light by the white light system 100.

It is next determined if the optical energy interacting with the optical filter 120 is within the transmitted spectrum (step 230). If the optical energy is not within the transmitted spectrum, it is next determined from what direction the optical energy came from (step 235). If the optical energy that is not in the transmitted spectrum entered (or interfaced with) the optical filter back face 122, then the optical energy is reflected back into the LED optical source 110 (step 210). In the example, since the LED does not provide optical energy within the optical filter spectrum, very little optical energy will be reflected according to this particular step, but for that associated with scattering. However, if it is determined (see step 235) the optical energy, that is not in the optical filter transmitted spectrum, entered (or interfaced with) the optical filter front face 122, then the optical energy reflects back into the phosphor layer 135 to interact with the phosphor layer (step 245).

On the other hand, if it is determined (see step 230) that the optical energy interacting with the optical filter 120 is within the transmitted spectrum, then it must next be determined what direction the optical energy came from (step 240). If the optical energy that is within the transmitted spectrum entered (or interfaced with) the optical filter back face 122, then the optical energy transmits through the optical filter 120 and into the phosphor layer 135 to interact with the phosphor layer (step 245). However, if the optical energy that is within the transmitted spectrum entered (or interfaced with) the optical filter front face 121, then the optical energy transmits through the optical filter 120 and into the LED optical source 110 (step 210)

Next, it is determined if the optical energy that enters (or interacts with) the phosphor layer is within the stimulated spectral width (step 250). The optical energy that interacts with the phosphor layer 135 that is not within the stimulated spectral width passes through the phosphor layer and exits the phosphor layer through the phosphor layer front face 136 (step 255)

For the optical energy that enters (or interacts with) the phosphor layer 135 that is within the stimulated spectral width, it is next determined if the optical energy is absorbed by the phosphor (step 260). If the optical energy that enters (or interacts with) the phosphor layer 135 and is within the stimulated spectral width is not absorbed by the phosphor, the optical energy transmits through the phosphor layer 135 and exits the phosphor layer through the phosphor layer front face 136 (step 265).

If the optical energy that enters (or interacts with) the phosphor layer 135 and is within the stimulated spectral width is absorbed by the phosphor, then new optical energy is created (step 270) (i.e., phosphor created optical energy). The phosphor created optical energy is at a spectral width that is different than the optical energy that was absorbed by the phosphor. In addition. the phosphor created optical energy has a $4\pi$ steradian angular distribution. Accordingly, the phosphor created optical energy emits out of the phosphor layer front face 136 and the phosphor layer back face 137. The amount of absorption is determined by, for example, but not limited to. the amount of phosphor doping, the thickness of the phosphor layer, the concentration of the phosphor particles within the suspension medium, etc. In a preferred embodiment of the invention, the amount of absorption is regulated to optimize a desired CCT range. CRI value, and/or optical energy produced by the white light system 100.

For the phosphor created optical energy, it is next determined if the optical energy emits out the phosphor layer front face 136 (step 275). If the phosphor created optical energy emits out the phosphor layer front face 136, then the optical energy passes through to the concentrator entrance aperture 142 (Step 280). If the phosphor created optical energy emits out the phosphor layer back face 137, then the optical energy transmits to the optical filter front face 121 (Step 285) and interacts with the optical filter (i.e., reflect or transmit) (step 225).

There are three aforementioned paths that optical energy exits phosphor layer front face 136, namely, from optical energy outside the stimulated range (see step 255), from non-absorbing optical energy within the stimulated range (see step 265), and phosphor created optical energy (see step 280) and enters the concentrator entrance aperture 142. In a preferred embodiment of the invention, the combination of the optical energy originating from these three paths, when properly mixed within the concentrator 140, produce white light. In addition, in an alternative embodiment of the invention, the contribution of optical energy from each path is modified to optimize a desired CCT range, CRI value, and/or optical energy produced by the white light system 100.

The concentrator 140 aligns and outputs the optical energy captured by way of the aforementioned three paths (step 290). In addition, the concentrator 140 mixes the optical energy captured at the concentrator entrance aperture 142 in so that the optical energy emitted by the concentrator exit aperture 141 is spatially uniform. The nature of the non-imaging concentrator is to transfer optical energy from one point to another and from one angular region to another. The non-imaging aspects of the concentrator provide mixing of the spatial distribution of the optical energy at the entrance aperture 142 such that the spatial distribution at the exit aperture 141 is uniform.

The emitted optical energy from the concentrator exit aperture 142, if left unobstructed, forms a diverging conical shaped first illumination region (step 292). The optical energy in the first illumination pattern then interacts with a secondary optical element 160, which modifies the optical energy in the first illumination pattern (step 294) to form a second illumination pattern (step 296).

EXAMPLE

Referring to FIG. 1, in a preferred embodiment of the invention, the LED optical source 110 is a combination of two LED optical sources. The first LED optical source 110 is an array of eight CREE Xbright Power Chip LED C470-XB900, which requires 1,125 milliwatts of electric power (i.e., 350 milliamps at 3.5 volts) to produce 150 milliwatts of optical power from each LED for optical energy with a spectral width of 440 nanometers to 480 nanometers and a spectral peak at 460 nanometers. The total optical power for the first LED optical source is therefore 1,350 milliwatts. The first LED optical source represents the stimulated optical energy. The second LED optical source 110 is one Lumileds HWFR-B515, which requires 700 milliwatts of electric power (i.e. 250 milliamps at 2.8 volts) to produce 150 milliwatts of optical power from the LED for optical energy with a spectral width of 620 nanometers to 660 nanometers and a spectral peak at 640 nanometers. The second LED optical source represents the non-stimulated optical energy. The total optical power for the combination of the First and second LED optical sources is therefore 1,500 milliwatts. The optical energy emits a two pi steradian angular distribution at the LED optical source front face 111 and the LED optical source back face 112. A reflector 130 is placed at the LED optical source back face 112 to reflect the two pi steradian angular distribution back into the LED and out through the LED optical source front face 111, minus any loss due to scattering and absorption, etc., thereby increasing the optical energy. The reflector has a reflected spectral width of 380 nanometers to 750 nanometers.

In a preferred embodiment of the invention, the optical filter 120 is coated on the LED optical source front face and the optical filter reflects optical energy between 500 nanometers to 750 nanometers and transmits optical energy between 380 nanometers and 500 nanometers. In a preferred embodiment of the invention, the optical filter reflects and transmits optical energy according to the a particular reflected spectrum width and a particular transmitted spectral width from both the optical filter front face 121 and the optical filter back face 122. In other words the filtering characteristics for the optical filter 120 are the same, independent on what direction the optical energy enters (or interacts with) the filter. In the example, since the LED provides optical energy between 440 nanometers and 480 nanometers, the LED optical source 110 created optical energy will pass through the optical filter back face 122 and into phosphor layer 135 unencumbered, but for nominal absorption and scattering losses.

In a preferred embodiment of the invention, the phosphor layer 135 is a mixture of phosphor and UV curable epoxy. The phosphor is Phosphor Technologies CS:YAG and the UV curable epoxy is Masterbond UTV 15-7. The phosphor layer 135 is 0.254 millimeters thick and has a phosphor doping population of one part phosphor in twenty parts epoxy by weight. In the continuing example, the phosphor layer has a stimulated spectral peak of 470 nanometers, a non-stimulated spectral peak of 640 nanometers and when stimulated, produces optical energy over a 4 pi steradian angular distribution with a spectral width of 500 nanometers to 750 nanometers, with a spectral peak of 550 nanometers and emits out of the phosphor layer back face 137 and the phosphor layer front face 136.

The optical energy created by the phosphor layer 135 that is emitted out of the phosphor layer back face 137 (i.e., within spectral width 500 nanometers to 750 nanometers) reflects off of the optical filter front face 121 (i.e., since the optical energy is within the reflected spectrum of the optical filter) and then interacts with the phosphor layer 135. Since the reflected optical energy is within the spectral width of 500 nanometers to 750 nanometers, the optical energy transmits through the phosphor layer 135 and exits through the phosphor layer front face 136, but for optical energy lost due to absorption and scattering. In a preferred embodiment of the invention, Side loss, within the phosphor layer 135, is reduced by coating the side walls with reflective material.

In the example, a small proportion of optical energy will exit the phosphor layer back face 137 within the spectral width of 380 nanometers to 500 nanometers due to scattering during the interaction with the phosphor layer 135. However, this energy is ultimately redirected by the white light system 100. Specifically, this optical energy (i.e., within spectral width 380 nanometers to 500 nanometers) transmits through the optical filter 130 (i.e., enters the optical filter front face 121, transmits through the filter, and exits through the optical filter back face 122), enters the LED optical source 110, and then reflects off of the reflector 130 (since the reflector 1A has a reflected spectrum of 380 nanometers to 750 nanometers). The reflected optical energy then travels back through the LED optical source 110, through the optical filter 130, and then interacts with the phosphor layer 135. This telescoping circular path for the optical energy contributes to the optical power (intensity), the CCT range, and the CRI value associated with the optical energy emitting out of the phosphor layer front face 136 at each revolution.

In addition, a partial amount optical energy within the phosphor layer stimulated spectral width will not be absorbed by the phosphor layer and pass through the phosphor layer and exit at the phosphor layer front face 136. The five paths of optical energy, the revolving path, the stimulated and absorbed path, the stimulated but not absorbed path, the non stimulated path, and the optical filter reflected path all contribute to the optical energy, the CCT range, and the CRI value associated with the optical energy emitting out of the phosphor layer front face 136.

The phosphor layer emits 450 milliwatts of optical energy with a two pi steradian distribution out the phosphor layer front face 136 with a spectral width of 440 nanometers to 730 nanometers with a primary peak at 460 and 640 nanometers (i.e., primarily from the LED created optical energy) and a secondary peak at 550 nanometers (i.e., primarily from the phosphor layer created optical energy), which produces a CCT (7300K) of 4200K and a CRI value of 92, which corresponds to white light.

Then, the concentrator entrance aperture 142 captures the two pi steradian optical energy emitting from the phosphor layer front face 136, mixes and aligns the optical energy, and then emits 432 milliwatts of spatially uniform white light with a CCT of 4200K and a CRI value of 92, into a diverging first illumination region 150.

The optical energy in the first illumination pattern then interacts with a secondary optical element 160. which modifies the optical energy in the first illumination region (step 294) to form a second illumination region (step 296). In a preferred embodiment of the invention, the second illumination region contains a target 180, which is illuminated with optical energy present in the second illumination region 170.

Figure 3:
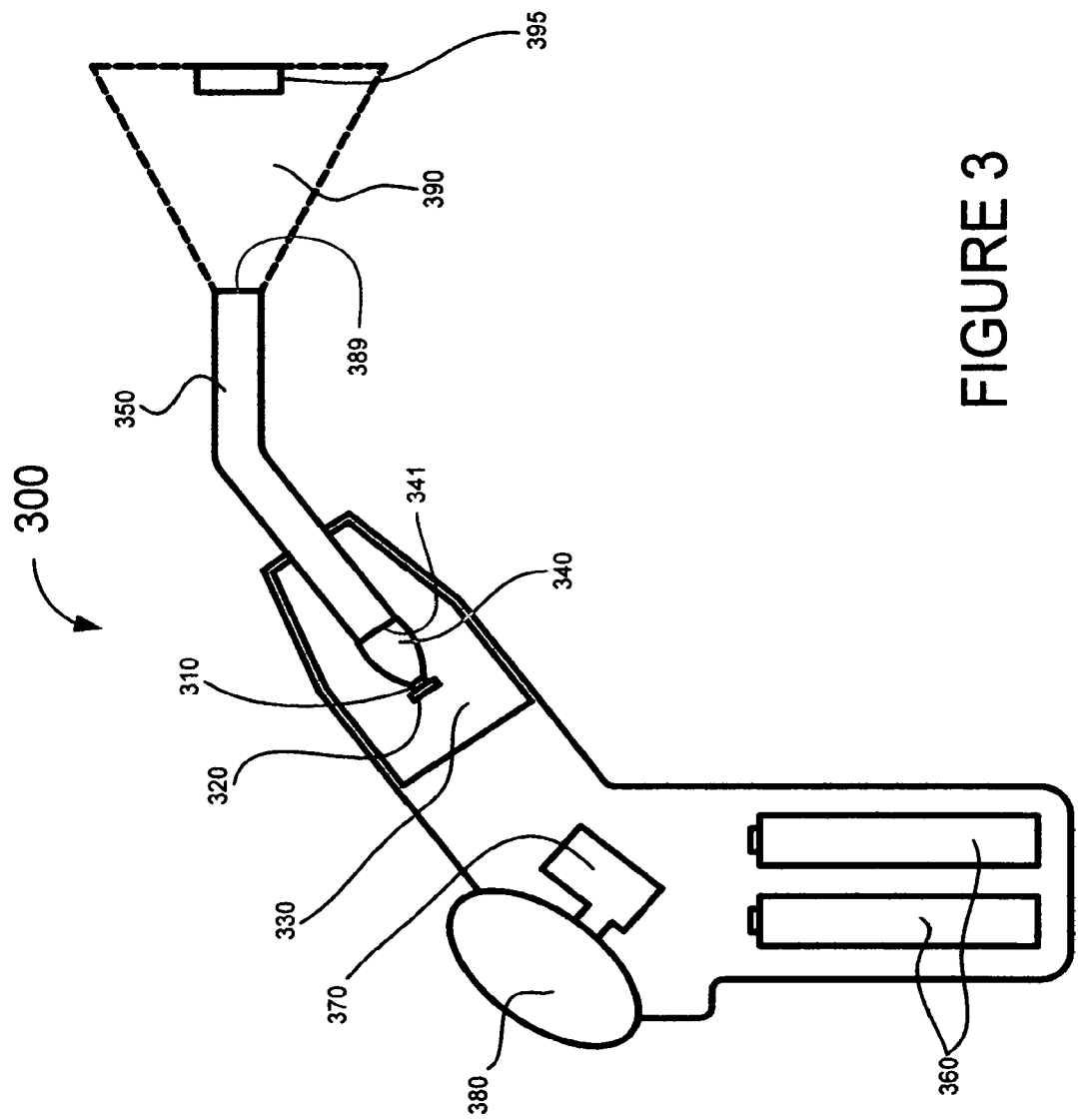
FIG. 3 illustrates a LED curing system according to an alternative embodiment of the invention.

FIG. 3 illustrates a LED curing system 300 according to a preferred embodiment of the invention for curing, bonding, and/or sealing light sensitive targets. The LED curing system 300 includes a LED optical source 310, a heat spreader 320, a heat sink 330, a concentrator 340, a light guide 350, power source 360, electronic controls 370, and a cycle controller 380, an illumination region 390, and a target 395.

LED optical source 310 is optically coupled to concentrator 340. LED optical source 310 includes a LED, which emits optical energy over a $4\pi$ steradian angular distribution, at a particular CCT range, at a particular wavelength spectrum and at a particular intensity. The CCT range includes the visible light spectrum, the ultraviolet light spectrum and the infrared light spectrum.

In an alternative embodiment, the LED optical source 310 includes a back reflector to capture additional optical energy and direct the optical energy to the concentrator 340. In an alternative embodiment of the invention, the LED optical source includes an array of LED's. In a preferred embodiment of the invention, optical requirements of the illumination region 390 determine the type, quantity and location of the LED's within the array that are located within the LED optical source 310.

In an alternative embodiment of the invention, the LED optical source 310 includes an array of LED's, which are positioned in an optimal location to increase thermal dissipation. In an alternative embodiment of the invention, the LED optical source 310 includes an array of LED's, which are positioned in an optimal location to obtain a desired CCT range in the illumination region 390. In an alternative embodiment of the invention, LED optical source 310 emits optical energy that matches the absorption CCT range of a particular light curing material.

In an alternative embodiment of the invention, the LED optical source 310 is optimized to satisfy particular thermal energy requirements of the LED curing system 300. Many curing systems are utilized in medical environments, which are sensitive to thermal energy (i.e., increase temperature).

The heat spreader 320 is thermally attached to the LED optical source 310 and pulls the thermal energy away from the thermal energy source (i. e., the LED optical source 310). Increased thermal dissipation provides for increased electric efficiency within the LED. In a preferred embodiment of the invention, the heat spreader 320 material includes diamond. Diamond has a high thermal conductivity and thus permit higher operating currents to be used without increasing the temperature of the LED. In an alternative embodiment of the invention, the heat spreader 320 material includes any material with a high conductivity, such as, but not limited to copper, aluminum, etc. The heat spreader 320 is thermally attached to the heat sink 330.

The heat sink 330 is thermally attached to the heat spreader. In an alternative embodiment, the heat sink 330 acts a casing for the LED curing system 330. In an alternative embodiment. the heat sink 330 acts as a light guide to guide optical energy present in the illumination region 390.

In an alternative embodiment, the heat sink 330 provides an integrating anchor for the light guide 350. In an alternative embodiment, the heat sink 330 is cooled by water to effectuate the dissipation of thermal energy. In an alternative embodiment, the heat sink 330 uses conductive cooling to dissipate thermal energy. In an alternative embodiment of the invention. the size, shape, and material of the heat sink is optimized to maximize the amount of thermal energy that the heat sink 330 dissipates.

The concentrator 340 is positioned to capture optical energy emitted from the LED optical source 310 and includes an entrance aperture and an exit aperture. Optical energy is received from the LED optical source 310 via the concentrator entrance aperture. The concentrator then aligns the received optical energy and then outputs the optical energy through the concentrator exit aperture to the light guide 350.

In a preferred embodiment of the invention, the concentrator 340 is a non-imaging concentrator. In a preferred embodiment of the invention, the concentrator 340 is a CPC shaped concentrator. In a preferred embodiment of the invention, the concentrator is flush with the LED optical source 310. In a preferred embodiment of the invention, the concentrator 340 includes a reflective coating on the inside surface to provide for an optically efficient transfer of optical energy from concentrator entrance aperture to the concentrator exit aperture. In a preferred embodiment of the invention, the concentrator 340 includes a dielectric material to provide for an optically efficient transfer of optical energy from concentrator entrance aperture to the concentrator exit aperture. In a preferred embodiment of the invention, any area between the LED light source 310 and the concentrator 340 is filled with an optically clear cement or gel to match the refractive index (e.g., when the concentrator is filled with a dielectric material.).

In a preferred embodiment of the invention, the concentrator is made of a dielectric material. In a preferred embodiment of the invention, the concentrator is made of a dielectric material that has a sufficient index of refraction to permit total internal reflection. In a preferred embodiment of the invention, the concentrator is made of a hollow reflector. In a preferred embodiment of the invention, the concentrator is made of a dielectric material.

The light guide 350 is positioned to receive aligned optical energy from the exit aperture of the concentrator 340. The light guide has an entrance aperture 341, which receives optical energy from the concentrator 340, and an exit aperture 389, which emits optical energy into an illumination region 390. In a preferred embodiment of the invention, the light guide 350 delivers the optical energy to an illumination region.

The power source 360 is electrically attached to the LED optical source 310 and provides electricity to the LED optical source 310. In a preferred embodiment of the invention, the power source 360 is a battery. In a preferred embodiment of the invention, the power source 360 is a hand held battery. In a preferred embodiment of the invention, the power source 360 is a battery that transfers 3,500 milliwatts of electrical power to the LED optical source. In a preferred embodiment of the invention, the power source 360 is positioned in the base of the LED curing system 300. To satisfy the curing application requirements, such as, but not limited to, CCT range intensity requirements, continuous use, etc., conventional systems use brute force (i.e., large optical sources, that emit large amounts of heat and require large amounts of power) since the conventional systems have poor electrical and optical efficiency. Thus, conventional systems cannot satisfy application requirements using a hand-sized off the shelf battery. In a preferred embodiment of the invention, the power source 360 is a rechargeable battery. In a preferred embodiment of the invention, the power source 360 is a wall plug.

The electronic controls 370 provide a user with control over the duration, the intensity and the CCT range of the optical energy emitted from the LED curing system 300 onto the target 395. In a preferred embodiment of the invention, the electronic controls can cycle on and off particular LED's within the LED optical source. In a preferred embodiment of the invention, the electronic controls can increase or decrease the electrical current to the LED optical source 310. In a preferred embodiment of the invention, the electronic controls can increase or decrease the electrical current to a particular LED within the LED optical source 310.

In a preferred embodiment of the invention, the electronic controls provide pulsing of the LED optical source 310 for a prescribed duty cycle. In a preferred embodiment of the invention, the electronic controls provide pulsing of the LED optical source 310 for a prescribed pulse duration. In a preferred embodiment of the invention, the electronic controls provide pulse width modulation ("PWM") of the LED optical source 310. PWM provides a constant drain on the power source as a function of the power source lifetime, which results in a constant output electrical power to the LED optical source 310 over the entire power source life cycle.

The cycle controller 380 is electrically attached to the power supply. Engaging the cycle controller 380 allows a user to initiate the LED curing system for one cycle. In a preferred embodiment of the invention, a cycle is ten seconds on and ten seconds off.

The illumination region is optically coupled to the light pipe 350. The illumination region begins at the exit aperture of the light pipe and continues in a diverging region. In a preferred embodiment of the invention, the optical power emitting at the exit aperture of the light pipe 350 is approximately ten to eighteen percent of the input electrical power.

The target 395 is positioned within the illumination region 390. In a preferred embodiment of the invention, the target 395 is positioned within the near field of the illumination region 390. In a preferred embodiment of the invention, the target includes a light sensitive material that cures when exposed to the optical energy within the illumination region 390.

In a preferred embodiment of the invention, the target includes a sealant that cures when introduced to the optical energy within the illumination region 390. In a preferred embodiment of the invention, the target includes an adhesive that cures when introduced to the optical energy within the illumination region 390. In a preferred embodiment of the invention, the target includes a composite that cures when introduced to the optical energy within the illumination region 390. In a preferred embodiment of the invention, the target includes light curing sealants used in lung surgery that cures when introduced to the optical energy within the illumination region 390.

In a preferred embodiment of the invention, the target includes light curing sealants used in dentistry when introduced to the optical energy within the illumination region 390. In a preferred embodiment of the invention, the target includes a composite used in dentistry that cures when introduced to the optical energy within the illumination region 390.

In a preferred embodiment of the invention, the target includes a light sensitive material for bonding that bonds when introduced to the optical energy within the illumination region 390. In a preferred embodiment of the invention, the target includes a light sensitive material for sealing that seals when introduced to the optical energy within the illumination region 390. In a preferred embodiment of the invention, the target includes a light sensitive material for bonding that bonds dental fixtures and/or dental implants when introduced to the optical energy within the illumination region 390. In a preferred embodiment of the invention, the target includes a light sensitive material for sealing that seals dental fixtures and/or dental implants when introduced to the optical energy within the illumination region 390. Light sensitive materials are used for bonding and/or sealing. For instance, the dental market has chosen light sensitive adhesives for bonding and sealing of dental fixtures and other dental implants.

In a preferred embodiment of the invention, the target includes adhesives that cure when introduced to ultra-violet optical energy within the illumination region 390. In a preferred embodiment of the invention, the target includes adhesive used in industrial applications that cures when introduced to ultra-violet optical energy within the illumination region 390 In a preferred embodiment of the invention, the target includes a biocompatible material that cures when introduced to the optical energy within the illumination region 390. In a prefer-red embodiment of the invention, the target includes a biocompatible material located topically that cures when introduced to the optical energy within the illumination region 390. In a preferred embodiment of the invention, the target includes a biocompatible material located within a body cavity that cures when introduced to the optical energy within the illumination region 390.

In an alternative embodiment of the LED curing system 300, the LED curing system 300 is portable. In an alternative embodiment of the LED curing system 300. the LED curing system 300 weighs 90 grams. In an alternative embodiment of the LED curing system 300. the LED curing system 300 has dimensions of 146 millimeters long by 18 millimeters diameter. In an alternative embodiment of the LED curing system 300, the LED curing system 300 is disposable.

Figure 4:
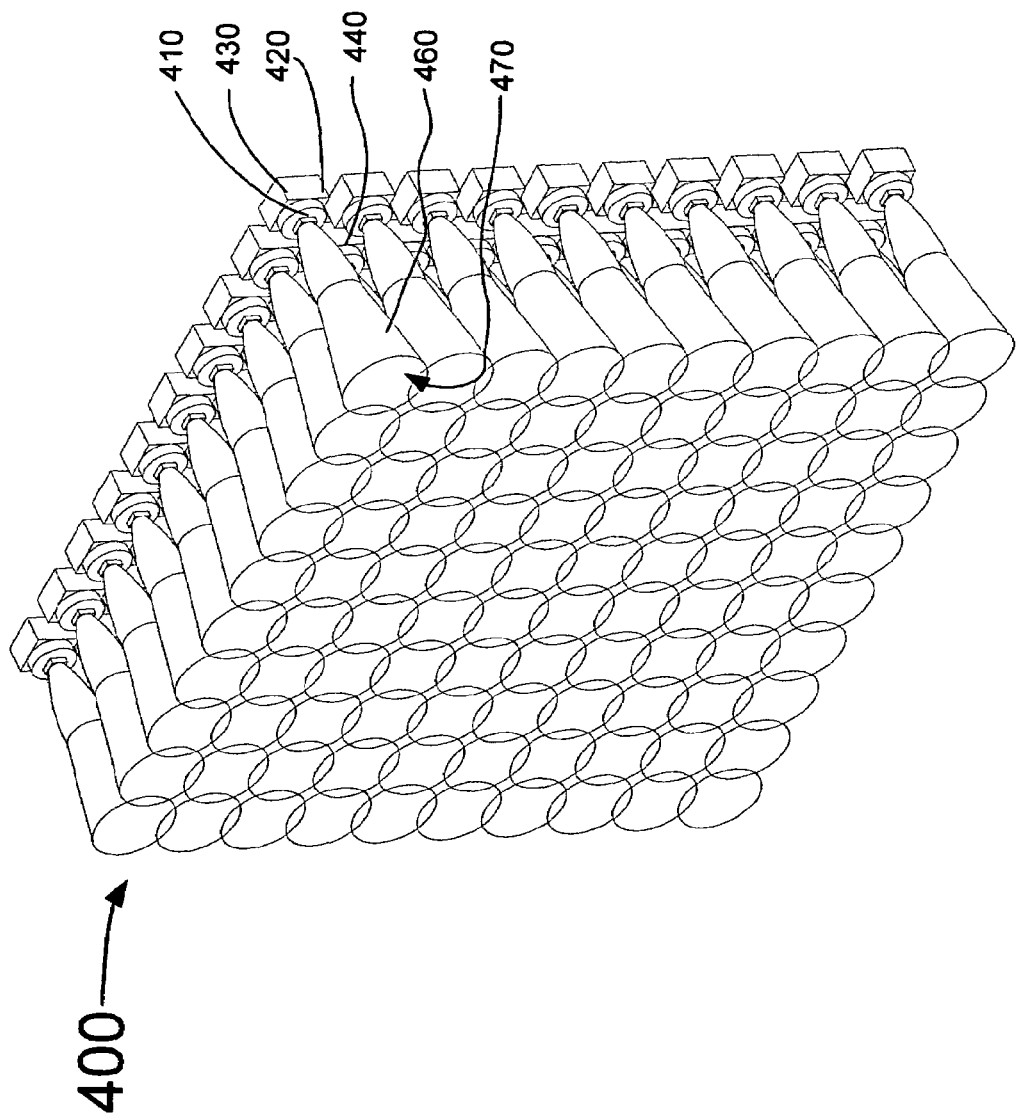
FIG. 4 illustrates a LED photodynamic therapy system according to an alternative embodiment of the invention.

FIG. 4 illustrates a LED photodynamic therapy system 400 according to a preferred embodiment of the invention. The LED photodynamic therapy ("PDT") curing system 400 includes a LED optical source 410, a heat spreader 420, a heat sink 430, a concentrator 440, power Source (not shown), an illumination region 460, a therapeutic region 470 and a target (not shown).

LED optical source 410 is optically coupled to concentrator 440. LED optical source 410 includes a LED, which emits optical energy over a $4\pi$ steradian angular distribution at a particular CCT range, a particular wavelength spectrum, and at a particular intensity. The CCT range includes the visible light spectrum, the ultraviolet light spectrum and the infrared light spectrum.

In an alternative embodiment, the LED optical source 410 includes a back reflector to capture additional optical energy and direct the optical energy to the concentrator 440. In an alternative embodiment of the invention, the LED optical source 410 includes an array of LEDs. In an alternative embodiment of the invention, optical requirements of the illumination region 460 determine the type, quantity and location of the LED that is located within the LED optical source 410.

In an alternative embodiment of the invention, the LED optical source 410 includes an array of LEDs, which are positioned in an optimal location to increase thermal dissipation. In an alternative embodiment of the invention, the LED optical source 410 includes an array of LEDs, which are positioned in an optimal location to obtain a desired wavelength spectrum in the illumination region 460. In an alternative embodiment of the invention, the LED optical source 410 includes an array of LEDs, which are positioned in an optimal location to obtain a desired wavelength spectrum in the illumination region 390.

In a preferred embodiment of the invention, the wavelength spectrum of the optical energy in the illumination region 460 is absorbed by a photosensitizer or drug compound. PDT involves injecting or doping biomaterial, such as, but not limited to, blood, cells, tissue, etc. with a photosensitizer or drug compound. Photosentizers and drug compounds, atoms, molecules, etc., responds to particular wavelengths of optical energy. When the photosensitizer or drug compound is exposed to a particular wavelength of optical energy, it absorbs the optical energy and emits a singlet oxygen or undergoes some other photochemical reaction. The singlet oxygen oxidizes critical elements of neoplastic cells (i.e., of the tumor cells). Thus, the wavelength spectrum of the optical energy within the illumination region 460 is determined by what wavelength will alter the photosensitizer (and, ultimately, the cell) or drug compound.

In a preferred embodiment of the invention, the wavelength spectrum of the optical energy in the illumination region 460 penetrates tissue located in the target 480. Optical energy with longer wavelengths penetrate tissue deeper than optical energy with shorter wavelengths. Thus, for example, the photosensitizer porfimer sodium has a peak absorption in the area of 405 nanometers (blue-violet) and another peak absorption in the area of 630 nanometers (red). Since red has a longer wavelength than blue-violet, the red optical energy will penetrate the tissue deeper than the blue-violet optical energy. Thus, the LED PDT system uses a LED optical system that produces optical energy with a peak at 630 nanometers.

In an alternative embodiment of the invention, LED optical source 410 emits optical energy that matches the absorption peak of a particular PDT photosensitizer. In an alternative embodiment of the invention, the optical energy produced by the LED PDT system corresponds to the absorption peak with the longest wavelength.

In an alternative embodiment of the invention, the LED optical source 410 is optimized to satisfy particular thermal energy requirements of the LED curing system 300. Many curing systems are utilized in medical environments, which are sensitive to thermal energy (i.e., increase temperature).

In an alternative embodiment of the invention, the LED is bonded to the heat spreader 420 with a thermally conductive material. In an alternative embodiment of the invention. the LED is soldered to the head spreader 420. In an alternative embodiment of the invention. the LED is bonded to the heat sink 430 with a thermally conductive material. In an alternative embodiment of the invention, the LED is soldered to the head sink 430.

The heat spreader 420 is thermally attached to the LED optical source 410 and pulls the thermal energy away from the thermal energy source (i.e., the LED optical source 410). Increased, thermal dissipation provides for increased electrical efficiency within the LED. In a preferred embodiment of the invention, the heat spreader 410 material includes diamond. Diamond has a high thermal conductivity and thus permits higher operating electrical currents to be used without increasing the temperature of the LED. In an alternative embodiment of the invention, the heat spreader 420 material includes any material with a high conductivity, such as, but not limited to copper, aluminum, etc. The heat spreader 420 is thermally attached to the heat sink 430.

The heat sink 430 is thermally attached to the heat spreader 420. In an alternative embodiment of the invention, the heat sink 430 acts as a casing for the LED PDT system 400. In an alternative embodiment, the heat sink 430 acts as a light guide to guide optical energy present in the illumination region 460.

In an alternative embodiment of the invention, the heat sink 430 is cooled by water to effectuate the dissipation of thermal energy. In an alternative embodiment, the heat sink 430 uses conductive cooling to dissipate thermal energy. In an alternative embodiment of the invention, the size, shape, and material of the heat sink is optimized to maximize the amount of thermal energy that the heat sink 430 dissipates.

The concentrator 440 is positioned to capture optical energy emitted from the LED optical source 410 and includes an entrance aperture and an exit aperture. Optical energy is received from the LED optical source 410 via the entrance aperture of the concentrator 440. The concentrator 440 then aligns the received optical energy and then outputs the optical energy through the exit aperture of the concentrator 440 to the illumination region 460.

In a preferred embodiment of the invention, the concentrator 440 is a non-imaging concentrator. In a preferred embodiment of the invention, the concentrator 440 is a compound parabolic concentrator ("CPC") shaped concentrator. In a preferred embodiment of the invention, the concentrator is flush with the LED optical source 410. In a preferred embodiment of the invention. the concentrator 440 includes a reflective coating on the inside surface to provide for an optically efficient transfer of optical energy from entrance aperture of the concentrator to the exit aperture of the concentrator. In a preferred embodiment of the invention, the concentrator transfers optical energy from the entrance aperture of the concentrator 440 to the exit aperture of the concentrator 440. In a preferred embodiment of the invention, any area between the LED optical source 410 and the concentrator 440 is filled with an optically clear cement or gel to match the refractive index (e.g., when the concentrator is filled with a dielectric material.).

In a preferred embodiment of the invention, the concentrator is made of a dielectric material. In a preferred embodiment of the invention, the concentrator is made of a dielectric material that has a sufficient index of refraction to permit total internal reflection. In a preferred embodiment of the invention, the concentrator is made of a hollow reflector. In a preferred embodiment of the invention, the concentrator is made of a dielectric material.

The power source (not shown) is electrically attached to the LED optical source 410 and provides electricity to the LED optical source 410. In a preferred embodiment of the invention, the power source is a battery. In a preferred embodiment of the invention, the power source is a hand held battery. In a preferred embodiment of the invention, the power source is a battery that transfers 600 watts of electrical power to the LED optical source. In a preferred embodiment of the invention, the power source is a rechargeable battery. In a preferred embodiment of the invention, the power source is a wall plug.

The illumination region is optically coupled to the exit aperture of the concentrator 440. The illumination region begins at the exit aperture of the concentrator and continues in a diverging region. In a preferred embodiment of the invention, the optical power emitting at the exit aperture of the light pipe 350 is approximately ten to eighteen percent of the input electrical power.

The therapeutic area is provided by an LED PDT system with multiple LED optical sources each with a dedicated concentrator, and each providing a unique illumination region. Each individual subsystem is referred to as a PDT light engine. In an alternative embodiment of the invention, the multiple illumination regions partially overlap.

The target (not shown) is positioned within the illumination region 460. The target is positioned within the therapeutic area 470. In a preferred embodiment of the invention, the target is positioned within the near field of the illumination region 460. In a preferred embodiment of the invention, the target is positioned within the far field of the illumination region 460.

In a preferred embodiment of the invention, the target includes a photosensitiser that undergoes a photochemical reaction when introduced to the optical energy in the therapeutic area 470. In a preferred embodiment of the invention, the target includes a drug compound that undergoes a photochemical reaction when introduced to the optical energy in the therapeutic area 470.

Figure 5:
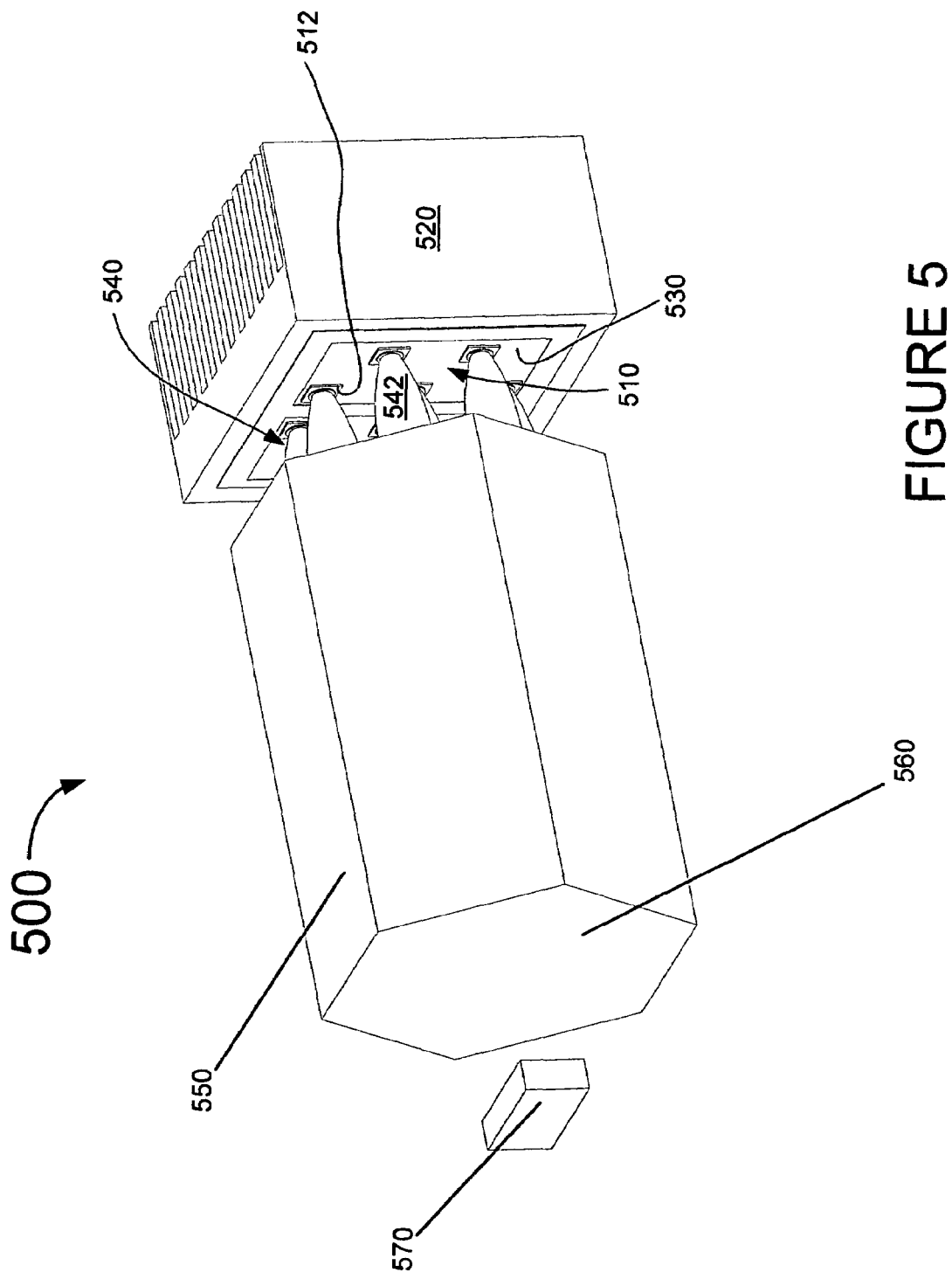
FIG. 5 illustrates a multi-wavelength LED array illumination system 500 according to an alternative embodiment of the invention.

FIG. 5 illustrates a multi-wavelength LED array illumination system 500 according to an alternative embodiment of the invention. The multi-wavelength LED array illumination system 500 includes a LED array 510, a heat sink 520, a ceramic board 530, an array of concentrators 540, a light integrator 550 and an illumination region 560 and a target 570.

The LED array 510 comprises LED groups 512. Each LED group comprises a single LED or an array of smaller LED's and emits optical energy over a 4π steradian angular distribution, at a particular CCT range, at a particular wavelength spectrum and at a particular intensity. The CCT range includes the visible light spectrum, the ultraviolet light spectrum and the infrared light spectrum. Each LED group 512 is optically coupled to a unique concentrator.

In an alternative embodiment of the invention, the wavelength spectrum emitted by each LED group 512 is the same. In an alternative embodiment of the invention, the LED groups 512 do not all emit the same wavelength spectrum. In an alternative embodiment of the invention, the wavelength spectrums emitted by each LED group 512 are optimized to provide a desired mix of wavelengths, such as, but not limited to, white light, or yellow light, etc. In an alternative embodiment of the invention, the LEDs are approximately 1.0 to 1.2 millimeters squared.

In an alternative embodiment of the invention, near field and far field color mixing is provided by distributing those LED groups 512, which emit like wavelength spectrums, throughout the LED array 510. In an alternative embodiment of the invention, the intensity of each LED group can be individually monitored. In an alternative embodiment of the invention, the intensity of each LED group 512 can be individually increased, decreased, turned off or turned on. In an alternative embodiment of the invention, the intensity of each LED within each LED group 512 can be individually increased, decreased, turned off or turned on.

In an alternative embodiment of the invention, the LED's within each LED group 512 includes a back reflector to capture additional optical energy and direct the optical energy to a corresponding concentrator. In an alternative embodiment of the invention, optical requirements of the illumination region 560 determine the type, quantity and location of the LED's within LED array.

In an alternative embodiment of the invention, the LED groups 512 are positioned in an optimal location to increase thermal dissipation. In an alternative embodiment of the invention, the LED groups 512 are positioned in an optimal location to obtain a desired CCT range in the illumination region 560.

The heat sink 520 is thermally attached to each LED group 512. In an alternative embodiment of the invention, the LED within each LED group 512 are thermally attached to the heat sink 520 by a thermally conductive material, such as, but not limited to solder, conductive epoxy, etc.

In an alternative embodiment of the invention, the heat sink 520 is cooled by water to effectuate the dissipation of thermal energy. In an alternative embodiment of the invention, the heat sink 520 uses conductive cooling to dissipate thermal energy. In an alternative embodiment of the invention, the size, shape, and material of the heat sink is optimized to maximize the amount of thermal energy that the heat sink 520 dissipates.

In an alternative embodiment, the heat sink 520 anchors the multi-wavelength LED array illumination system 500 to a host, such as, but not limited to a mechanical device, a human, a casing, etc.

In an alternative embodiment of the invention, the heat sink includes fins. Fins provide greater surface area for increased thermal energy dissipation. In an alternative embodiment of the invention, forced convection is used to dissipate thermal energy from the multi-wavelength LED array illumination system 500 and, more specifically, thermal energy from the heat sink 520 and/or thermal energy from each LED group 512.

In an alternative embodiment of the invention, the heat sink 520 material includes copper. In an alternative embodiment of the invention, the heat sink 520 material includes aluminum. In an alternative embodiment of the invention, the heat sink 520 material includes material that has a high thermal and electrical conductivity.

In an alternative embodiment of the invention, a heat spreader is positioned between the heat sink 520 and the LED groups 512. A heat spreader pulls the thermal energy laterally away from the thermal energy source (i. e., the LED groups 512) and, thus, decreases the effective heat flux (heat power/unit area) impingent upon the heat sink 520. Increased thermal dissipation provides for increased electric efficiency within the LED groups 512. In a preferred embodiment of the invention, the heat spreader material includes diamond. Diamond has a high thermal conductivity (relative to the heat sink 512). In an alternative embodiment of the invention, the heat spreader material includes any material with a high conductivity, such as, but not limited to copper, aluminum, etc. In a preferred embodiment of the invention, the heat spreader is thermally attached to the heat sink 520.

The ceramic board 530 provides an electrical path to the LED's within the LED groups 512. The ceramic board is mounted on the heat sink 520 and provides cut-outs through which the LED's within the LED groups 512 are mounted to the heat sink 520. The ceramic board includes metalized traces. In an alternative embodiment of the invention, a heat spreader contains a cutout or window which provide the LED groups electrical contact to the ceramic board 530 and the heat sink 520.

In an alternative embodiment of the invention, the N-type electrical contact is directly bonded to the heat sink 520. In an alternative embodiment of the invention, the N-type electrical contact is wire bonded to the heat sink 520 from the top of the LED die within the LED group 512. In an alternative embodiment of the invention, the P-type contacts are wire bonded to electrical traces located on the ceramic board 530. An electrical power source is electrically connected to the heat sink 520.

The array of concentrators 540 includes an individual concentrator 542 for each LED group 512 Each concentrator 542 is optically coupled to the corresponding LED group 512.

Each concentrator 542 is positioned to capture optical energy emitted from each LED group 512 and includes an entrance aperture and an exit aperture. Optical energy is received from each LED group 512 via the entrance aperture of each concentrator 542. Each concentrator 542 then aligns the received or captured optical energy from the corresponding LED group 512 and then outputs the aligned optical energy through the exit aperture of each concentrator 542.

In a preferred embodiment of the invention, each concentrator 542 is a non-imaging concentrator. In a preferred embodiment of the invention, each concentrator 542 is a CPC concentrator. In a preferred embodiment of the invention, each concentrator 542 is flush with the corresponding LED groups 512.

In an alternative embodiment of the invention, a non-imaging concentrator 542 is constructed with a high order polynomial surface representing the attributes of the non-imaging concentrator form. In an alternative embodiment of the invention, the aspheric sag equation is tuned to match an appropriate non-imaging concentrator form. In an alternative embodiment of the invention, any mathematical representations that approximate the ideal non-imaging concentrator provides the concentrator profile.

In a preferred embodiment of the invention, each concentrator 542 includes a reflective coating on the inside surface to provide for an optically efficient transfer of optical energy from the entrance aperture of each concentrator 542 to the exit aperture of each concentrator 542. In a preferred embodiment of the invention, the concentrator 542 includes a dielectric material to provide for an optically efficient transfer of optical energy from the entrance aperture of each concentrator 542 to the exit aperture of each concentrator 542. In a preferred embodiment of the invention, any area between the each LED group 512 and each corresponding concentrator 542 is filled with an optically clear cement or gel to match the refractive index (e.g., when the concentrator is filled with a dielectric material.).

In a preferred embodiment of the invention, each concentrator 542 includes a dielectric material. In a preferred embodiment of the invention, each concentrator 542 includes a dielectric material that has a sufficient index of refraction to permit total internal reflection. In a preferred embodiment of the invention, each concentrator 542 is made of a hollow reflector. In a preferred embodiment of the invention, each concentrator 542 is made of a dielectric material.

In an alternative embodiment of the invention, the array of concentrators 540 includes nineteen concentrators. In a preferred embodiment of the invention, the nineteen concentrators 542 are positioned in hexagonal close pack array. The position of the concentrators dictates the positions of the LED groups.

A single LED and single concentrator system that emits the same to similar optical power as the LED and concentrator array system uses the same amount of electrical power. However, by using an array of LED's and concentrators, the thermal energy created by the LED's is more easily dissipated due to the geometrical distribution of the LEDs' positions. In other words, the single system has large focused amount of thermal energy at one point (i.e., the thermal flux is isolated in one spot), whereas the array system has smaller amounts of optical energy disbursed over numerous locations (i.e., the heat flux is spread out). Furthermore, since array system more efficiently dissipates heat, the optical power is not reduced due to electrical inefficiency when compared the optical power created by the single system.

In an alternative embodiment of the invention, the LED and concentrator array system when compared to a system with one LED and one concentrator and provide same to similar amounts of optical power and angular distribution, the LED and concentrator array system is significantly shorter than the single LED and once concentrator system.

In an alternative embodiment of the invention, a phosphor layer is placed between a concentrator 542 and light group 512. The phosphor layer creates optical energy at a specific wavelength range when stimulated by optical energy of a different wavelength range. In an alternative embodiment of the invention, the use of a phosphor layer is used to optimize the output wavelength of the multi-wavelength LED array illumination system 500.

The light pipe 550 is optically coupled to the exit apertures of the array concentrators 542. The multi-sided light pipe that interfaces to the array of concentrators, assures that the near field intensity at its output will be uniformly distributed over its exit face. In an alternative embodiment of the invention, the far field intensity is uniform when the entrance apertures of the array of concentrators 542 are uniformly filled.

In an alternative embodiment of the invention, the optical efficiency of the multiwavelength LED array illumination system 500 is optimized by positioning the LED and concentrator array in the same shape as the entrance aperture of the light pipe.

In an alternative embodiment of the invention, the light pipe 550 mixes the optical energy from the exit apertures of each concentrator 542. In an alternative embodiment of the invention, the light pipe is faceted, which optimizes the mixing efficiency. A circular light pipe is a poor mixer of optical energy. A faceted light pipe is a more efficient mixer than a circular light pipe. However, the higher the number of facets, the closer the circumference approaches a circle, the mixing efficiency wanes. In addition, a light pipe with an even number of facets is a more efficient mixer than a light pipe with an odd number of facets. The optimum number of facets (i.e. for optimum mixing) is eight. In an alternative embodiment of the invention, the light pipe 550 has eight facets or sides. In order to fully benefit from the optimal mixing efficiencies, however, the entrance aperture of each concentrator in the array must be fully filled and the array shape must correspond to the hexagonal shape of the light pipe. In an alternative embodiment of the invention, the LED and concentrator array is hexagonal in shape. In an alternative embodiment of the invention, the entrance aperture of each concentrator 543 is fully filled. In an alternative embodiment of the invention, the light pipe 550 is hexagonal.

In an alternative embodiment of the invention, the array of concentrators 540 is molded as one unit. Molding the concentrators together reduce optical losses. In an alternative embodiment of the invention, the array of concentrators 540 and the light pipe are all molded together as one unit.

In an alternative embodiment of the invention, any optical element that directs or modifies optical energy is optically coupled to the exit apertures of the concentrators 542 in the array of concentrators 540.

In an alternative embodiment of the invention, the multi-wavelength LED array illumination system 500 includes a single concentrator. In an alternative embodiment of the invention, the multi-wavelength LED array illumination system 500 includes a prism to capture and direct the optical energy exiting the exit aperture of a single concentrator. In an alternative embodiment of the invention, the prism directs optical energy orthogonally.

The illumination region 560 is optically coupled to exit face of the light pipe 550. The illumination region begins at the exit face of the light pipe. In a preferred embodiment of the invention, the optical power emitting at the exit aperture of the light pipe 350 is approximately ten to eighteen percent of the input electrical power. In an alternative embodiment of the invention, the illumination region 560 is optically coupled to the exit apertures of each concentrator 542. In an alternative embodiment of the invention, the illumination region 560 is optically coupled to a single exit aperture.

The target 570 is positioned within the illumination region 560. In a preferred embodiment of the invention, the target 570 is positioned within the near field of the illumination region 560.

In an alternative embodiment of the invention, the multi-wavelength LED array illumination system 500 produces white light. In an alternative embodiment of the invention, LED array 510 includes a blue LED, a red LED, and a green LED to produce white light in the illumination region 560. In an alternative embodiment of the invention, blue LED is cycled off and the remaining red LED and green LED combine to produce yellow light. In an alternative embodiment of the invention, yellow light (i.e., fog lights) is instantly produced from white light by turning off the blue LED.

The longer wavelength yellow color does not scatter as much as the shorter wavelength blue color. The scattering of the light through the water particles reduces visibility when driving in foggy or rainy conditions.

In an alternative embodiment of the invention, the multi-wavelength LED array illumination system 500 produces optical energy with a CCT range of 4100K to 4900K and a CRI value of 92, both of which satisfy the major surgical lighting industry requirements.

In an alternative embodiment of the invention, the multi-wave length LED array illumination system 500 provides illumination for automotive lighting which includes, but is not limited to, automotive head lights, automotive secondary head lights, automotive fog lights, automotive indicator lights. In an alternative embodiment of the invention, the multi-wavelength LED array illumination system 500 provides optical energy source for automotive illumination lighting and automotive indicator lighting, etc.

In an alternative embodiment of the invention, the multi-wavelength LED array illumination system 500 provides illumination for medical lighting which includes, but is not limited to, overhead (or major) surgical lighting, endoscope illumination at the distal end, surgical head lights. PDT illumination, and an UV Bilirubin blanket.

In an alternative embodiment of the invention, the multi-wavelength LED array illumination system 500 provides optical energy for dental field applications which include, but are not limited to, curing, tooth whitening, illumination for a portable head light, illumination for intra-oral cameras, etc.

In an alternative embodiment of the invention, the multi-wavelength LED array illumination system 500 provides optical energy for consumer applications which include, but are not limited to, head lighting, bike lighting, high end flashlights, an automotive trouble light, a light therapy box, and a miner's head light, etc.

In an alternative embodiment of the invention, the multi-wavelength LED array illumination system 500 provides optical energy for safety applications, which include, but are not limited to, strobe lighting, beacons, etc.

In an alternative embodiment of the invention, the multi-wavelength LED array illumination system 500 provides optical energy for industrial applications which include, but are not limited to, machine vision lighting, display lighting, UV spot curing light, decorative lighting system, food inspection equipment.

While the invention has been described in terms of preferred embodiments, those skilled in the art will recognize that the invention can be practiced with modifications within the spirit and scope of the appended claims.

What is claimed is:

1. Apparatus for irradiating targets to change their properties, said apparatus comprising:
    at least one LED having a predetermined spectral output that is at least in part capable of interacting with a target to effect changes in its properties, said output being emitted from said LED over a predetermined solid angle;
    a non-imaging concentrator for collecting radiation emitted by said LED and re-emitting substantially all said collected radiation as a beam having a diverging solid angle smaller than said predetermined solid angle over which radiation is emitted by said LED, said non-imaging concentrator having an entrance aperture for receiving radiation emitted by said LED and an exit aperture from which said LED output emerges spatially and spectrally uniform in the near field of said exit aperture, said non-imaging concentrator having a shape that continuously enlarges from said entrance aperture to said exit aperture thereof; and
    a light guide having an entrance aperture optically coupled to said exit aperture of said non-imaging concentrator for receiving radiation therethrough and conducting it to an exit aperture thereof from which radiation is emitted to irradiate a target.

2. The apparatus of claim 1 wherein said LED comprises an array of LEDs.

3. The apparatus of claim 2 wherein said array of LEDs comprises LEDs having differing spectral outputs.

4. The apparatus of claim 3 further including electronic means for selectively controlling the timing and supply of electrical current to individual ones of said LEDs to control their intensity and duty cycle and thus the spectral content of said LED output delivered to said non-imaging concentrator entrance aperture.

5. The apparatus of claim 4 wherein said electronic means comprises a pulse width modulator (PWM) for controlling the duty cycle of said LEDs.

6. The apparatus of claim 4 further including a user interface for interacting with said electronic means for selectively controlling the intensity, color content, and duty cycle of said LEDs.

7. The apparatus of claim 3 wherein said array of LEDs comprises LED having spectral outputs with content in the ultraviolet, visible, and/or infrared regions of the spectrum.

8. The apparatus of claim 1 wherein said LED has front and back surfaces each of which emits radiation over a solid angle of $2\pi$ steradians.

9. The apparatus of claim 8 further including a reflector positioned upstream of said back surface of said LED to intercept radiation emitted by said back surface and redirect it downstream where in can be used at least in part to contribute to said LED output.

10. The apparatus of claim 1 further including a heat sink for dissipating heat generated in the process of converting electrical energy to optical power to enhance the quantum efficiency of said apparatus.

11. The apparatus of claim 10 further including a heat spreader for distributing heat to said heat sink.

12. The apparatus of claim 11 wherein said heat spreader comprises a thin layer of diamond.

13. The apparatus of claim 1 wherein said output radiation of said apparatus is capable of making chemical and physical changes in targets selected from the group of materials including UV curable adhesives, dental bonding material, heat sensitive materials, surgical adhesives, and light curing sealants.

14. The apparatus of claim 1 further including a hand-held portable housing.

15. The apparatus of claim 14 wherein said hand-held, portable housing is configured and arranged to releasably retain batteries for powering said apparatus.

16. The apparatus of claim 14 wherein said hand-held portable housing is equipped with a power cord for accepting line power for said apparatus.

17. The apparatus of claim 14 wherein said apparatus weighs approximately 90 grams.

18. The apparatus of claim 17 wherein said apparatus measures approximately 146 millimeters long.

* * * * *